United States Patent
Sutters et al.

(10) Patent No.: US 12,340,878 B2
(45) Date of Patent: Jun. 24, 2025

(54) METHODS AND SYSTEMS FOR CONVERTING UNSTRUCTURED DATA INTO AN ENCODED, STRUCTURED REPRESENTATION

(71) Applicant: McKesson Corporation, Irving, TX (US)

(72) Inventors: Steven Sutters, Irving, TX (US); Era Prakash, Irving, TX (US); Entela Duka, Irving, TX (US)

(73) Assignee: McKesson Corporation, Irving, TX (US)

( * ) Notice: Subject to any disclaimer, the term of this patent is extended or adjusted under 35 U.S.C. 154(b) by 446 days.

(21) Appl. No.: 17/554,714

(22) Filed: Dec. 17, 2021

(65) Prior Publication Data

US 2023/0197210 A1    Jun. 22, 2023

(51) Int. Cl.
*G16H 10/20*    (2018.01)
*G06F 40/103*   (2020.01)
*G16H 10/60*    (2018.01)

(52) U.S. Cl.
CPC ........... *G16H 10/20* (2018.01); *G06F 40/103* (2020.01); *G16H 10/60* (2018.01)

(58) Field of Classification Search
CPC .............................. G16H 10/20; G16H 10/60
See application file for complete search history.

(56) References Cited

U.S. PATENT DOCUMENTS

| | | | |
|---|---|---|---|
| 10,109,027 B1* | 10/2018 | Stack | G06Q 50/22 |
| 10,366,780 B2* | 7/2019 | Dorsett | G16H 10/20 |
| 2013/0197935 A1 | 8/2013 | Obst et al. | |
| 2019/0189289 A1* | 6/2019 | Sarkar | G16H 50/70 |
| 2021/0090694 A1* | 3/2021 | Colley | G16H 15/00 |
| 2021/0248150 A1* | 8/2021 | Stockton | G16H 10/20 |
| 2021/0374876 A1* | 12/2021 | Cedergreen | G06Q 10/10 |

OTHER PUBLICATIONS

K. Milian, A. Bucur and A. Ten Teije, "Formalization of clinical trial eligibility criteria: Evaluation of a pattern-based approach," 2012 IEEE International Conference on Bioinformatics and Biomedicine, Philadelphia, PA, USA, 2012, pp. 1-4, doi: 10.1109/BIBM.2012.6392733 (Year: 2012).*
TriNetX "Trials and Evidence" available at https://trinetx.com/life-sciences/ pp. 1-7 (accessed on Feb. 23, 2022).

* cited by examiner

*Primary Examiner* — Joshua B Blanchette
(74) *Attorney, Agent, or Firm* — Ballard Spahr LLP

(57) ABSTRACT

Methods, systems, and apparatuses are described for computationally converting unstructured data into an encoded, structured representation. Methods, systems, and apparatuses are described for patient recruitment for clinical trials.

20 Claims, 12 Drawing Sheets

FIG. 7

Company Name

Clinical Trial Prescreen Form

Lorem ipsum dolor sit amet, consectetur adipiscing elit. Massa massa amet malesuada consectetur adipiscing non tristique amet. Dictum enim, Macenas id ist. Enim in tristique feugiat eu rhoncus a mattis. At risus, scelerisque mollis amet.

PRESCREENER QUESTIONS

First Name _____  Last Name _____

Address 1 _____

City _____  State ____  Zip ____

[CONTINUE]

Requests

Account

Logout

FIG. 8

Company Name

BACK

Clinical Trial Prescreen Form

Lorem ipsum dolor sit amet, consectetur adipiscing elit. Massa massa amet malesuada consectetur adipiscing non tristique amet. Dictum enim, Macenas id ist. Enim in tristique feugiat eu rhoncus a mattis. At risus, scelerisque mollis amet.

PATIENT INFORMATION

Is the potential participant 18-55 years of age?
- ○ Yes
- ○ No

Has the potential participant been diagnosed with [insert diagnosis here]?
- ○ Yes
- ○ No Is the potential participant willing to comply with the study schedule?
- ○ Yes
- ○ No Requests Account Logout

FIG. 9

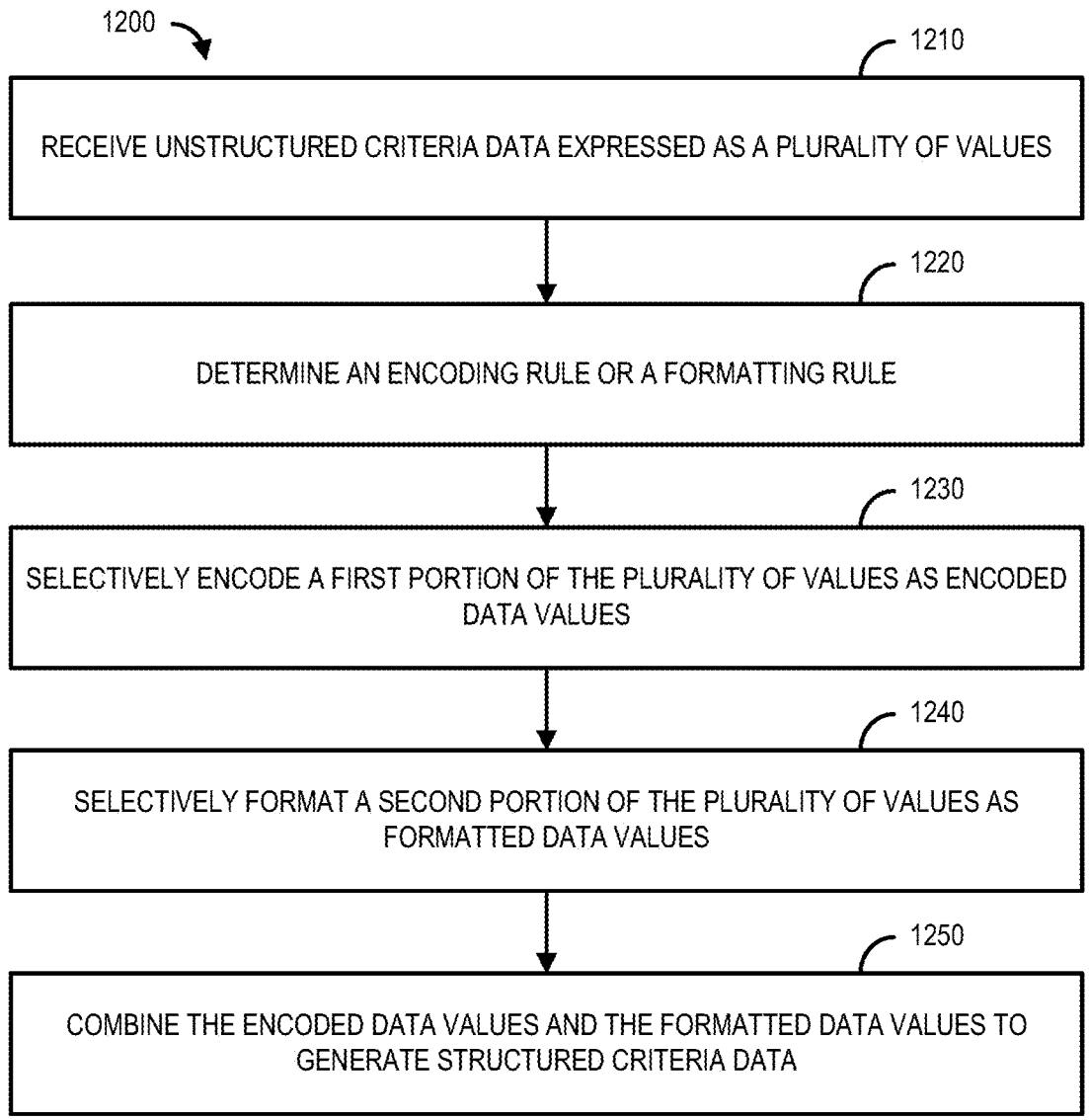

METHODS AND SYSTEMS FOR CONVERTING UNSTRUCTURED DATA INTO AN ENCODED, STRUCTURED REPRESENTATION

BACKGROUND

In the biotechnology and pharmaceutical industry, a critical part of drug development, genetic therapy and even medical device product development involves conducting a clinical trial, which is a carefully-managed medical test of a potential drug, therapy or device on a group of patients over a period of time. The clinical trial will generate information on the efficacy of the drug, therapy or device, as well as safety information on side effects and adverse reactions. Clinical trials are required in many countries before a drug, therapy or device can be used. In many cases, the clinical trial must provide certain levels of positive results if a drug, therapy or device is to be approved by a government agency for use by the general population.

Clinical trials are often conducted at a clinical site (medical practice office, hospital or specialized clinic) and require periodic participation by the patients over a long period of time, from as little as a few days to many years. The patients are required to come to the clinical site numerous times for long periods of time to receive treatments and be tested to determine the results of the treatments.

As a result, finding patients to participate in the clinical trial is a significant challenge. A clinical trial must find patients who appear to be suffering from a condition which the drug, therapy or device is intended to treat. Finding a specific population of people in a high enough concentration within one area may be exceedingly difficult, and convincing an eligible patient to participate is yet another challenge. Many clinical trials provide monetary incentives from a few hundred to several thousand dollars to participate in a clinical trial. Even when a group of patients that meet certain criteria are enrolled and begin a treatment, patients may drop out or quit participating for any number of reasons. For example, some patients may not be able to follow the rigorous treatment and examination schedules, while some patients may enroll in a clinical trial simply for the monetary benefit and otherwise be a bad candidate for the particular clinical trial being conducted. As a result of the above, along with numerous other factors, patient recruitment consumes more time and money than any other aspect of drug development.

The biotechnology and pharmaceutical industries are therefore in need of ways to not only reduce the costs of clinical trials, but to also reduce delays in patient recruitment while also obtaining patients which provide the best chance for an accurate result and study completion. These and other shortcomings are addressed by the present disclosure.

SUMMARY

Methods, systems, computer readable media, and apparatuses are described that are configured for performing a method comprising receiving, by a service provider computing device, from a healthcare provider computing device associated with a prescriber, a healthcare request associated with a patient, sending, based on the healthcare request, a prescription request to a pharmacy claims processor computing device for processing, determining, based on the healthcare request, patient data associated with the patient, determining, based on the patient data and clinical trial protocol data, a clinical trial for which the patient may be a candidate, identifying, based on the patient data and the clinical trial protocol data, the patient for participation in a clinical trial associated with the clinical trial protocol data, receiving, based on the prescription request, from the pharmacy claims processor computing device, a prescription response, and sending a notification to the healthcare provider computing device indicating that the patient has been identified for participation in the clinical trial and the prescription response.

Methods, systems, computer readable media, and apparatuses are described that are configured for performing a method comprising receiving unstructured criteria data expressed as a plurality of values, determining, for the plurality of values, an encoding rule or a formatting rule, selectively encoding, based on the encoding rule, a first portion of the plurality of values as encoded data values, selectively formatting, based on the formatting rule, a second portion of the plurality of values as formatted data values, and combining, based on a structure rule, the encoded data values and the formatted data values to generate structured criteria data.

Additional advantages will be set forth in part in the description which follows or may be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

FIG. 7 illustrates an example user interface.
FIG. 8 illustrates an example user interface.
FIG. 9 illustrates an example user interface.
FIG. 12 illustrates an example method.

DETAILED DESCRIPTION

Figure 1:
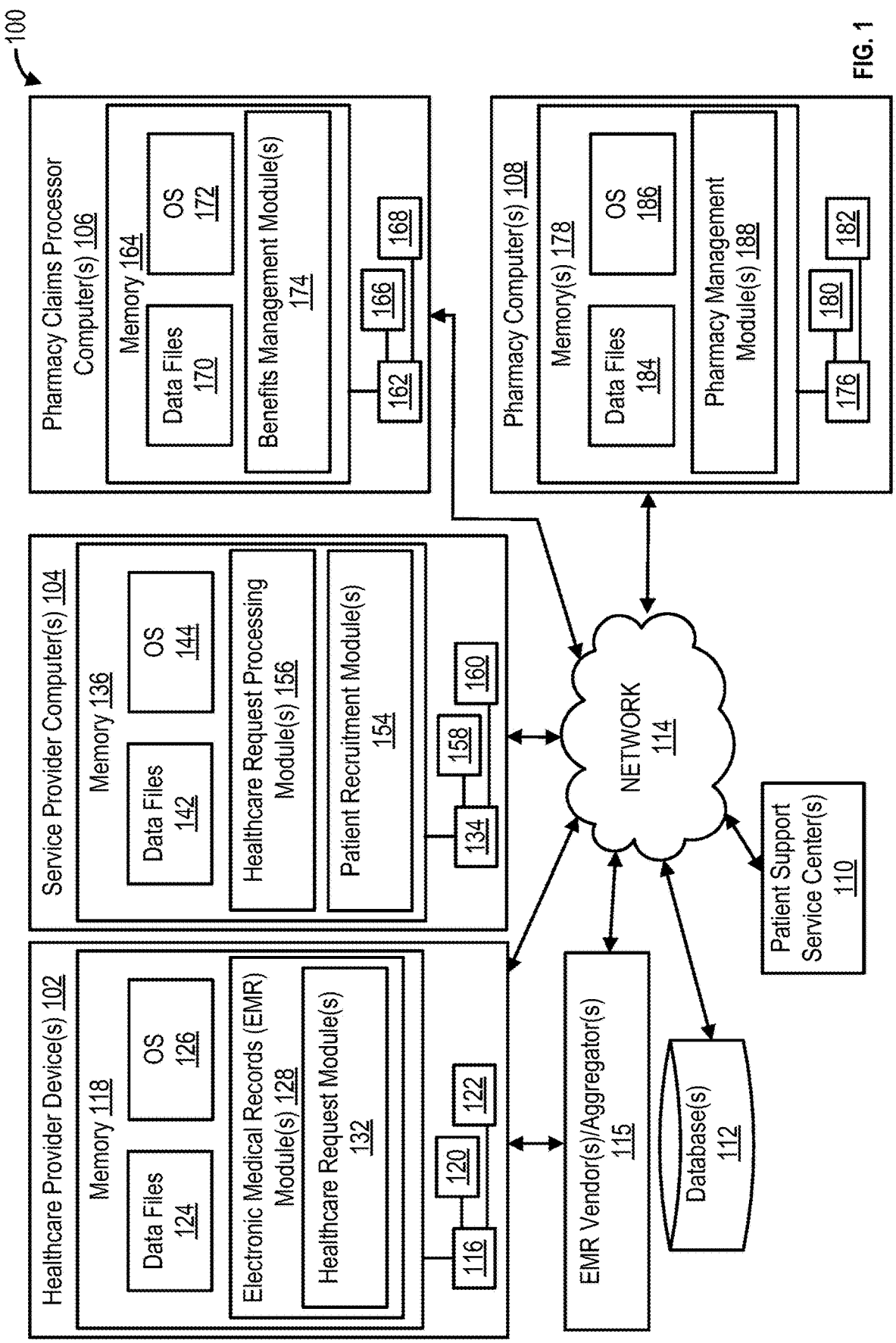
FIG. 1 illustrates an example system.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an" and "the" include plural referents unless the context clearly dictates otherwise. Ranges may be expressed herein as from "about" one particular value, and/or to "about" another particular value. When such a range is expressed, another embodiment includes—from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems may be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium may be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions may be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Hereinafter, various embodiments of the present disclosure will be described with reference to the accompanying drawings. As used herein, the term "user" may indicate a person who uses an electronic device or a device (e.g., an artificial intelligence electronic device) that uses an electronic device.

Systems and methods provide for recruiting and matching patients for clinical trials using a network-based software platform which publicizes clinical trials, recruits patients for participation in the clinical trials, and obtains patient profile information to match patients with appropriate clinical trials based on medical and behavioral compatibility.

Exemplary embodiments described herein include systems and methods for identification of patients as candidates for participation in one or more clinical trials. In an embodiment, the systems and methods may be configured to identify a patient as a candidate for participation in one or more clinical trials in conjunction with determining and communicating patient pay information or prescription benefit coverage denial information to a prescriber during the prescribing process. In an embodiment, the systems and methods may be configured to identify a patient as a candidate for participation in one or more clinical trials in after the prescribing process, for example, in conjunction with a patient support center or "hub."

In an embodiment, while a prescriber is determining which medication to prescribe to a patient during a prescribing process a healthcare request (e.g., a prescription benefit check request and/or a prior authorization request) may be communicated (either directly or indirectly via an EMR vendor/aggregator system) from a healthcare provider computer associated with a healthcare provider (e.g., a prescriber (e.g., a doctor, dentist, nurse, nurse practitioner, hospital, or clinic) of products, services, or medications) and received by a service provider computer. In one example, the healthcare request may include pharmacy benefit information captured by a healthcare provider during a patient visit. For example, the healthcare provider may capture the patient's name, date of birth, gender, preferred pharmacy identification, and benefits provider identification (e.g., pharmacy benefits manager, healthcare or pharmacy benefits insurance provider, government healthcare insurance provider, etc.). Additionally, the healthcare request may include one or more identifications of the medication to be prescribed to the patient. In some examples, the healthcare request may be communicated in real-time or near real-time to the service provider computer. The service provider computer may determine a request type of the healthcare request. In some implementations, the request type may include, without limitation, a pharmacy request (e.g., a pharmacy billing request (e.g., request type "B1"), a billing request (e.g., request type "P1"), or a predetermination of benefits request (e.g., request type "D1")) formatted under an NCPDP Telecom standard. The service provider computer may also access pharmacy information captured in a previously submitted prescription request determined to meet one or more predetermined pharmacy and medication qualifiers.

The service provider computer may process the healthcare request as described in U.S. Pat. Nos. 10,417,380; 10,742,654; U.S. Pat. Pub. No. 2011/0257992; U.S. Pat. Pub. No. 2017/0004282; and/or U.S. Pat. Pub. No. 2017/0046492, each of which is incorporated by reference in their entireties. The service provider computer may, in response to the healthcare request, identify whether the patient is a candidate for a clinical trial. The service provider computer may send a notification that the patient is a candidate for a clinical trial to a healthcare provider computer, to a patient support service center, and/or to a patient computer. The service provider computer may be configured to analyze data including, but not limited to, medication data, condition data, socio-economic data, geographic data, and/or demographic data, to identify and/or pre-screen candidates.

In an embodiment, a notification may be provided to the healthcare provider in the prescribing workflow notifying them of the patient's identification as a candidate for one or more clinical trials. Should the healthcare provider wish to proceed, a pre-screener interactive form custom to the selected clinical trials may be presented to pre-screen the patient for the selected clinical trials. A research coordinator and/or physician may receive the notification and/or may conduct a pre-screen of a patient identified as a candidate for the selected clinical trials. Successfully pre-screened patients may be referred to the clinical trial site for final screening and enrollment.

In an embodiment, a patient service provider, such as a patient support service center (or "hub"), may receive the notification and conduct pre-screening through phone outreach to candidates on behalf of the healthcare provider. Successfully pre-screened patients may be referred to the clinical trial site for final screening and enrollment.

In an embodiment, a notification may be provided directly to the patient. For example, through an application installed on a patient mobile device, an SMS or text message sent to the patient that directs the patient to a pre-screening application/website, and the like. The notification may be provided directly to the patient according to systems and methods described in U.S. patent application Ser. No. 16/945,408, filed Jul. 31, 2020, which is incorporated by reference in its entirety. Successfully pre-screened patients may be referred to the clinical trial site for final screening and enrollment.

FIG. 1 illustrates an example system 100 configured to facilitate identification of one or more patients as candidates for one or more clinical trials and may facilitate recruitment of the one or more patients into the one or more clinical trials. The example system 100 may also be configured for facilitating an electronic prior authorization (ePA) process and/or determination of and communication of patient pay information or prescription benefit coverage denial information to a prescriber (e.g., during a process of selecting a medication to be prescribed to the patient), according to one example embodiment of the disclosure.

As shown in FIG. 1, the system 100 may include one or more prescriber and/or healthcare system devices 102, service provider computers 104, pharmacy claims processor computers 106, pharmacy computers 108, patient support service computers 110, and/or EMR vendor/aggregator systems 115. As desired, each of the prescriber and/or healthcare provider devices 102, service provider computer 104, pharmacy claims processor computers 106, pharmacy computers 108, patient support service computers 110, and/or EMR vendor/aggregator systems 115 may include one or more processing devices that may be configured for accessing and reading associated computer-readable media having stored data thereon and/or computer-executable instructions for implementing various embodiments of the disclosure.

As shown in FIG. 1, the one or more prescriber and/or healthcare provider devices 102, service provider computers 104, pharmacy claims processor computers 106, pharmacy computers 108, patient support service computers 110, and/or EMR vendor/aggregator systems 115 may be in communication with each other via one or more networks, such as network 114, which may include one or more independent and/or shared private and/or public networks including the Internet or a publicly switched telephone network. In other example embodiments, one or more components of the system 100 may communicate via direct connections and/or communication links. Each of these components—the prescriber and/or healthcare provider device 102, service provider computer 104, pharmacy claims processor computer 106, pharmacy computers 108, patient support service computers 110, EMR vendor/aggregator system 115, and the network 114—will now be discussed in further detail. Although the components are generally discussed as singular components, as may be implemented in various example embodiments, in alternative exemplary embodiments each component may include any number of suitable computers and/or other components.

The example healthcare provider device 102 is not intended to be limited to physician's offices alone and may otherwise be associated with any healthcare provider, such as, for example, a prescriber (such as a hospital, urgent care center, clinic, dentist, etc.), a pharmacist, a research coordinator, combinations thereof, and the like. While the example healthcare provider device 102 references a physician's office, this is for example only and is not intended to be limiting in any manner.

With continued reference to FIG. 1, one or more prescriber and/or healthcare provider devices 102 may be associated with a prescriber of medication (e.g., physicians, dentists, nurse practitioners, hospitals, physicians offices, clinics, or any other person or entity legally authorized to prescribe medications, products, or services to patients) and/or healthcare provider, for example, a physician, a nurse, a nurse practitioner, a physician's assistant, a hospital, a physician's office, a clinic, a dentist, etc. A prescriber and/or healthcare provider device 102 may be any suitable processor-driven device that facilitates the processing of healthcare requests. Healthcare requests may include, for example, a prescription benefit check request and/or an electronic prior authorization request (e.g., an electronic prior authorization initiation request, an electronic prior authorization request, an electronic prior authorization appeal request, and/or an electronic prior authorization cancel request formatted under the NCPDP Script Standard for example). Healthcare requests may be made by or on behalf of, for example, a physician's office for a patient prescription. The prescriber and/or healthcare provider device 102 may be configured to communicate (either directly or indirectly via the EMR vendor/aggregator system 115) a health care request to the service provider computer 104, and/or receive, process, and display of a response to a healthcare request received (either directly or indirectly via the EMR vendor/aggregator system 115) from the service provider computer 104. A response to a health care request may be, for example, a prescription benefit check response, an electronic prior authorization initiation response, electronic prior authorization response, electronic prior authorization appeal response, and electronic prior authorization cancel response formatted under the NCPDP Script Standard.

The prescriber and/or healthcare provider device 102 may be a computing device that includes any number of server computers, mainframe computers, networked computers, desktop computers, personal computers, mobile devices, smartphones, digital assistants, personal digital assistants, tablet devices, Internet appliances, application-specific integrated circuits, microcontrollers, minicomputers, and/or any other processor-based devices. The prescriber/healthcare provider device 102 having computer-executable instructions stored thereon may form a special-purpose computer or other particular machine that is operable to facilitate the processing of electronic requests for healthcare information made by or on behalf of a prescriber and/or healthcare provider and the electronic transmittal of requested healthcare information, electronic prior authorization requests, and other electronic healthcare requests to the service provider computer 104. Additionally, in certain example embodiments, the operations and/or control of the prescriber/healthcare provider device 102 may be distributed among several processing components. In addition to including one or more processors 116, the prescriber/healthcare provider device 102 may further include one or more memory devices (or memory) 118, one or more input/output ("I/O") interfaces 120, and one or more network interfaces 122. The memory devices 116 may be any suitable memory devices, for example, caches, read-only memory devices, random access memory devices, magnetic storage devices, removable storage devices, etc. The memory devices 118 may store data, executable instructions, and/or various program modules utilized by the prescriber/healthcare provider device 102, for example, data files 124, an operating system ("OS") 126, and/or an electronic medical records (EMR) module 128. The OS 126 may be a suitable software module that controls the general operation of the prescriber/healthcare provider device 102. The OS 126 may also facilitate the execution of other software modules by the one or more processors 116, for example, the EMR module 128. The OS 126 may be any operating system known in the art or which may be developed in the future including, but not limited to, Microsoft Windows®, Apple OSX™, Apple iOS™ Google Android™, Linux, Unix, or a mainframe operating system.

The electronic medical records (EMR) module 128 may be a software application, including, but not limited to, a dedicated program: for making diagnoses; for determining prescriptions, over-the-counter medications, products, or other healthcare services associated with one or more diagnoses; for creating healthcare requests such as a prescription benefit check requests and/or an electronic prior authorization request; for reading and/or updating medical records, as well as interacting with the service provider computer 104 either directly or indirectly via the EMR vendor/aggregator system 115. For example, a user, such as a prescriber or other healthcare system employee, may utilize the EMR module 128 of the prescriber/healthcare provider device 102 during a patient visit, for optionally capturing the patient's pharmacy benefit information. Furthermore, the prescriber/healthcare provider device 102 may utilize the EMR module 128 to retrieve or otherwise receive data, messages, or responses (either directly or indirectly via the EMR vendor/aggregator system 115) from the service provider computer 104 and/or other components of the system 100.

The EMR module 128 may engage a healthcare request module 132. The healthcare request module 132 may be a software application configured to communicate healthcare requests (e.g., electronic prior authorization requests) to the service provider computer 104 (either directly or indirectly via the EMR vendor/aggregator system 115) for use in determining whether the patient's benefits provider (e.g., via the pharmacy claims processor computer 106 or associated with the patient's benefits provider) or prior authorization clearinghouse will approve the electronic prior authorization request and display the electronic prior authorization response and potentially additional patient or medication related messaging information to the prescriber for communication to the patient. The healthcare request module 132 may gather all the required and available optional data including, but not limited to, the medication/product/service information (e.g., total number of medications, medication name(s), NDC code(s), RxNorm medication identifiers, medication or product quantity to be dispensed to the patient, days' supply, etc.), patient information (e.g., patient name, patient gender, patient date of birth, patient zip or other postal zone identifier), and prescriber identification number (i.e., prescriber ID ((e.g., NPI code, DEA number)), prescriber name, and prescriber ZIP code or other postal zone identifier. Following the information collection, the healthcare request module 132 formats one or more electronic prior authorization requests (e.g., an electronic prior authorization initiation request, an electronic prior authorization request, an electronic prior authorization appeal request, or an electronic prior authorization cancel request) for a patient prescription according to NCPDP Script Standards in the agreed upon format. The electronic prior authorization request may then be electronically transmitted (either directly or indirectly via the EMR vendor/aggregator system 115) to the service provider computer 104 via the network 114.

The one or more I/O interfaces 120 may facilitate communication between the prescriber/healthcare provider device 102 and one or more input/output devices, for example, one or more user interface devices, such as a display, keypad, control panel, touch screen display, remote control, mouse, microphone, etc., that facilitate user interaction with the prescriber/healthcare provider device 102. For example, the one or more I/O interfaces 120 may facilitate entry of information associated with an electronic prior authorization requests by a prescriber or other healthcare provider, such as a physician. The one or more network interfaces 122 may facilitate connection (either directly or indirectly via the EMR vendor/aggregator system 115) of the prescriber/healthcare provider device 102 to one or more suitable networks, for example, the network 114 illustrated in FIG. 1. In this regard, the prescriber/healthcare provider device 102 may electronically receive and/or transmit (either directly or indirectly via the EMR vendor/aggregator system 115) information to other network components of the system 100, such as the service provider computer 104.

With continued reference to FIG. 1, the system 100 may include any number of EMR vendor/aggregator systems 115. Each EMR vendor/aggregator system 115 may be associated with any number of prescriber/healthcare provider devices and computer systems 102. For example, each EMR vendor/aggregator system 115 can be a vendor of EMR programs and systems provided to multiple prescribers/healthcare providers and/or an aggregator of EMR data from the multiple prescribers/healthcare providers and can act as a conduit for electronic requests and/or responses electronically communicated between the prescriber/healthcare provider device 102 and the service provider computer 104 via the network 114. In certain example embodiments, the EMR vendor/aggregator 115 provides a single-point access for the electronic transmission of data and electronic requests associated with or using a healthcare provider's electronic medical records system to the service provider computer 104 via the prescriber/healthcare provider device 102.

With continued reference to FIG. 1, one or more special-purpose service provider computers 104 may be associated with (e.g., located at or under the control of) a service provider. The service provider computer 104 is a processor-driven device that is configured for electronically receiving, processing, and fulfilling requests from the one or more prescriber/healthcare provider computers 102, one or more pharmacy computers 108, the one or more pharmacy claims processor computers 106, the one or more patient support service computers 110, and/or one or more databases 112, relating to pharmacy, benefits, billing, electronic prescription delivery and submission, and/or other healthcare requests and/or other activities. The service provider computer 104 is a special purpose switch/router device that electronically routes healthcare requests, from a prescriber/healthcare provider computer 102 (either directly or via the EMR vendor/aggregator system 115) to a pharmacy claims processor computer 106.

The service provider computer 104 may include any number of special-purpose computers or other particular machines, application-specific integrated circuits, microcontrollers, personal computers, minicomputers, mainframe computers, servers, networked computers, and/or other processor-driven devices. In certain embodiments, the operations of the service provider computer 104 may be controlled by computer-executed or computer-implemented instructions that are executed by one or more processors associated with the service provider computer 104 to form a special-purpose computer or other particular machine that is operable to facilitate the receipt, routing, and/or processing of healthcare requests. The one or more processors that control the operations of the service provider computer 104 may be incorporated into the service provider computer 104 and/or may be in communication with the service provider computer 104 via one or more suitable networks. In certain example embodiments, the operations and/or control of the service provider computer 104 may be distributed among several processing components.

The service provider computer 104 may include one or more processors 134, one or more memory devices 136, one or more input/output ("I/O") interfaces 138, and one or more network interfaces 140. The one or more memory devices 136 may be any suitable memory device, for example, caches, read-only memory devices, etc. The one or more memory devices 136 may store data, executable instructions, and/or various program modules utilized by the service provider computer 104, for example, data files 140, an operating system ("OS") 144, a healthcare request processing module 156, and/or a patient recruitment module 154. The healthcare request processing module 156 and/or the patient recruitment module 154 may be operable to access one or more databases in database 112 or in another database communicably coupled to the service provider computer 104. In one example, the service provider computer 104 may have a dedicated connection to the database 112. However, the service provider computer 104 may also communicate with the database 112 via the network 114 shown, or via another network. The OS 144 may be any operating system known in the art or which may be developed in the future including, but not limited to, Microsoft Windows®, Apple OSX™, Linux, Unix, Apple iOS™, Google Android™, or a mainframe operating system. The OS 144 may be a suitable software module that controls the general operation of the service provider computer 104 and/or that facilitates the execution of other software modules.

The healthcare request processing module 156 may be a software application, including, but not limited to, a dedicated program configured for receiving electronic healthcare requests (including electronic prior authorization requests and/or prescription benefit check requests) from prescriber/healthcare provider computers 102 associated with (e.g., located within or otherwise under the control and administration of) prescribers of medication (e.g., physicians, dentists, nurse practitioners, hospitals, physicians offices, clinics, or any other person or entity legally authorized to prescribe medications, products, or services to patients) either directly or via an EMR vendor/aggregator system 115, and pharmacy computers 108 associated with (e.g., located within or otherwise under the control and administration of) pharmacies, conducting edit or analysis actions on the electronic healthcare requests, and, in some situations, forwarding the electronic healthcare requests to a pharmacy claims processor computer 106 associated with (e.g., located within or otherwise under the control and administration of) a pharmacy claims processor or benefits provider (e.g., pharmacy benefits manager (PBM), insurance provider, government insurance provider (e.g., Medicare, Medicaid)) or a prior authorization clearinghouse. The service provider computer 106 can be configured to electronically receive electronic healthcare responses from the pharmacy claims processor computers 108 and/or prior authorization clearinghouses, conduct editing or analysis actions on the electronic healthcare responses, and forward all or a portion of the data from the electronic healthcare response and/or modifying or generating new electronic healthcare responses and forwarding them electronically to the originating prescriber/healthcare provider computer 102 (either directly or via an EMR vendor/aggregator system 115).

The patient recruitment module 154 may be a software application, including, but not limited to, a dedicated program configured for, in response to receiving a healthcare request via the healthcare request processing module 156, identifying potential subjects for a clinical trial. In order to identify potential subjects for a clinical trial, one or more exclusion or inclusion criteria may be defined for the clinical trial. The one or more exclusion or inclusion criteria may take the form of unstructured criteria data. The exclusion or inclusion criteria may be associated with, for example, desired characteristics of a person (e.g., age, gender, weight, race, socio-economic status, geographic location, and the like), prescribed medication, and/or a targeted health condition (e.g., possessing a certain diagnosis or being associated with a medical diagnosis code, co-morbidity, and the like). Defining one or more exclusion or inclusion criteria may include selecting one or more medical diagnosis codes, one or more geographical areas (e.g., by zip code), one or more prescribed medication names, and the like.

Figure 2:
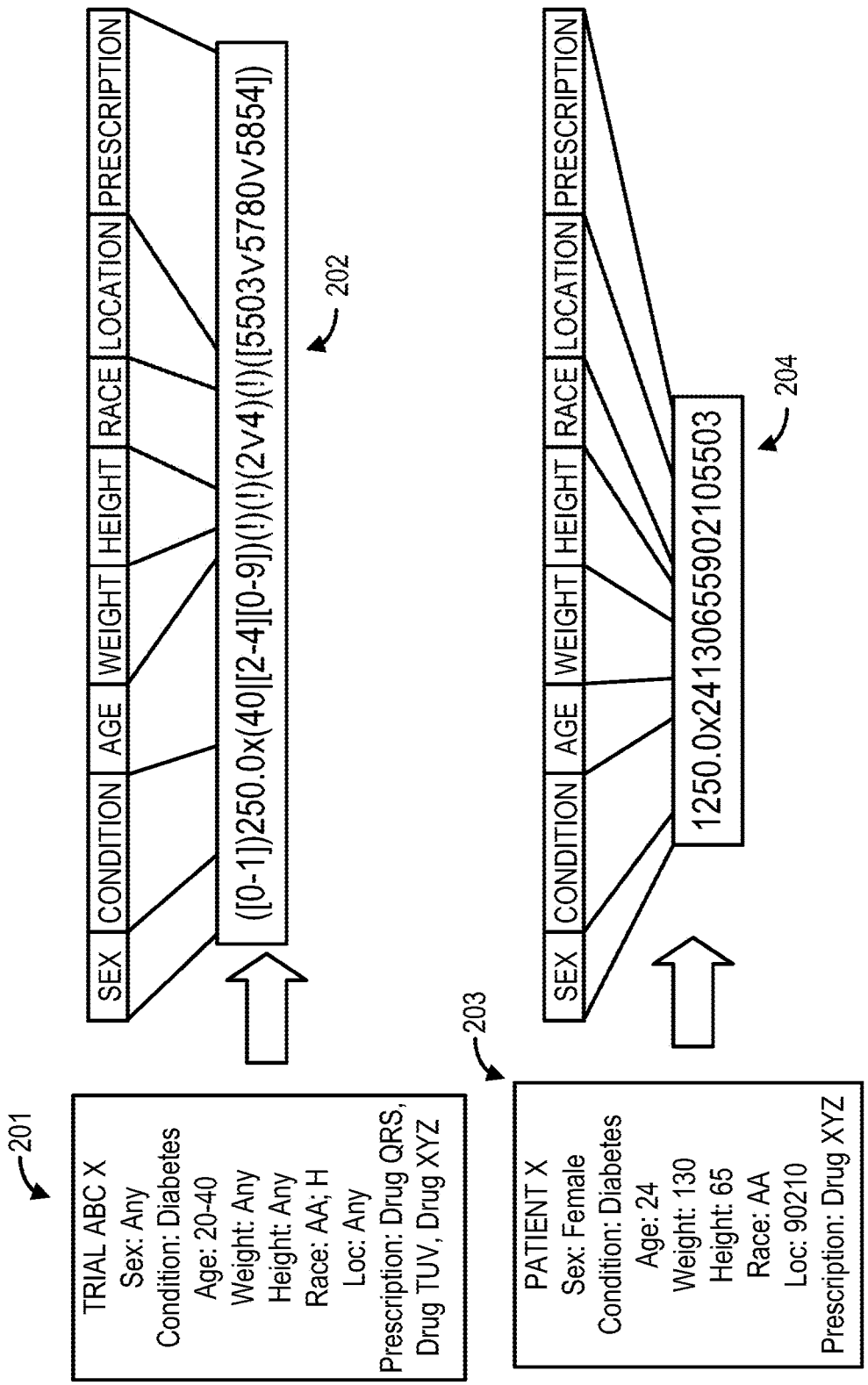
FIG. 2 illustrates example data.

Once defined, the one or more exclusion or inclusion criteria can be encoded (or not encoded) into a clinical trial protocol data structure as shown in FIG. 2. A rule may be defined based on a type of data value that reflects how a data value should be encoded, or if the data value should not be encoded, but rather formatted. The encoding rule may specify how to express a value as a regular expression based on a data value type. The formatting rule may specify how to express a value as a value based on a data value type. FIG.

2 shows criteria 201. Criteria 201 indicate that clinical trial "Trial ABC" requires patients that are of any sex, diagnosed with diabetes, between the ages of 20-40, any weight, any height, either African-American or Hispanic, located anywhere, and that are taking or being prescribed one or more of "Drug QRS," "Drug TUV," or "Drug XYZ." The patient recruitment module 154 may be configured to encode the criteria 201 into a clinical trial protocol data structure 202. Clinical trial protocol data structure 202 may be configured as a string or similar data structure. The criteria 201 may be encoded according to one or more encoding and/or formatting rules and concatenated according to a structure rule to form the clinical protocol data structure 202. The structure rule may specify an order in which encoded data values and formatted data values should be concatenated. Each criterion of the criteria 201 may be associated with a value. For example, for the "sex" criterion male may be equal to zero "0" and female may be equal to one "1." As the clinical trial requires patients of either sex, the sex criterion may be encoded as ([0-1]), indicating that either value (0 or 1) is a match. For example, the "condition" criterion may be represented as a code corresponding to one or more diagnoses (e.g., ICD-9 codes, ICD-10 codes, and the like). ICD-9 codes refer to the official system of assigning codes to diagnoses and procedures associated with hospital utilization in the United States. As the clinical trial requires patients of diagnosed with diabetes mellitus without mention of complications, the condition criterion may be encoded as (250.0x), the ICD-9 corresponding to diabetes mellitus without mention of complications. For example, the "age" criterion may be a number (e.g., an integer) greater than zero "0." As the clinical trial requires patients between the ages of 20-40, the age criterion may be encoded as (40|[2-4] [0-9]), indicating that any value between and including 20 to 40 is a match. For example, the "weight" criterion may be a number (e.g., an integer) greater than zero "0." As the clinical trial requires patients of any weight, the weight age criterion may be encoded as (!), indicating that any value is a match. For example, the "height" criterion may be a number (e.g., an integer) greater than zero "0." As the clinical trial requires patients of any height, the height criterion may be encoded as (!), indicating that any value is a match. For example, for the "race" criterion a plurality of races may each be assigned a numeric representation. For example, African-American may be assigned a value of "2" and Hispanic may be assigned a value of "4." As the clinical trial requires African-American or Hispanic patients, the race criterion may be encoded as (2V4), indicating that either a 2 or a 4 is a match. As the clinical trial requires patients located anywhere, the location criterion may be encoded as (!), indicating that any zip code value is a match. For example, for the "prescription" criterion a plurality of medications may each be assigned a numeric representation. For example, Drug QRS may be assigned a value of "5503," Drug TUV may be assigned a value of "5780," and Drug XYZ may be assigned a value of "5854." As the clinical trial requires patients that have been prescribed or taking one of at least Drug QRS, Drug TUV, or Drug XYZ, the prescription criterion may be encoded as (5503 V 5780 V 5854), indicating that any of Drug QRS, Drug TUV, or Drug XYZ is a match.

Once the healthcare request processing module 156 receives a healthcare request, patient information associated with the healthcare request may be determined and encoded into a patient query data structure. In an embodiment, the patient recruitment module 154 may be configured to convert the patient information according to the same or similar rules as were adhered to in order to encode criteria into a clinical trial protocol data structure. FIG. 2 shows patient information 203. The patient information 203 indicate that "Patient X" is a female, with diabetes, aged 24, weighing 130 pounds, 65 inches tall, African-American, located in zip code 90210, and currently prescribed Drug XYZ. The patient recruitment module 154 may be configured to encode the criteria 201 into a clinical trial protocol data structure 202. Clinical trial protocol data structure 202 may be configured as a string or similar data structure. The patient information 203 may be encoded (or in some instances not encoded) according to one or more rules and concatenated to form a patient query data structure 204. Each attribute of patient information 203 may be associated with a value. For example, for the "sex" attribute, Patient X is a female, which may be encoded as a one "1." For example, the "condition" attribute may be represented as a code corresponding to one or more diagnoses (e.g., ICD-9 codes). As Patient X is diagnosed with diabetes mellitus without mention of complications, the condition attribute may be encoded as (250.0x), the ICD-9 corresponding to diabetes mellitus without mention of complications. For example, for the "age" attribute, Patient X is 24, which value may be used in the patient query data structure 204. Similarly, weight and height represent integer values that may be used in the patient query data structure 204. For the "race" attribute, Patient X is African-American which may be encoded as two "2." For the "location" attribute, Patient X is located in zip code 90210, which value may be used in the patient query data structure 204. For the "prescription," Patient X is prescribed Drug XYZ which may be encoded as "5503."

In an embodiment, a prescribed medication may be mapped to a diagnosis. For example, in the event an ICD code is unavailable in the patient information 203, a diagnosis may be determined by determining whether a prescribed medication in the patient information 203 is a medication that is commonly prescribed for a condition. If the prescribed medication is commonly prescribed for a condition, then the condition may be used to identify the patient as a candidate for a clinical trial.

Once the patient query data structure 204 has been encoded, the patient recruitment module 154 may be configured to compare the patient query data structure 204 to one or more clinical trial protocol data structures 202 in order to determine one or more matches. Such comparison and matching represents an improvement over traditional search techniques by minimizing data reading, maximizing cache-line efficiency, and performing effective data compression. The amount of data required to store data associated with clinical trials and patient information suitable for searching against the data associated with clinical trials is significantly reduced. Moreover, once created, the patient query data structure 204 may be searched against clinical trial protocol data structures 202 as they are created, resulting in the potential to further expand and quickly recruit patients for clinical trials.

In an embodiment, a staged filtering technique may be used to match patient information to the one or more exclusion or inclusion criteria. Each item of patient information may be tagged in order of significance. Patient information may then be compared to the one or more exclusion or inclusion criteria according to the order of significance. For example, a prescribed medication may be ragged as most significant, location as second most significant, and gender as third most significant. Accordingly, any clinical trials that do not relate to the prescribed medication will be discarded without regard to matching any other items of the patient information. Of the clinical trials that do relate to the prescribed medication, any clinical trials that do not match the location of the patient will be discarded without regard to matching any other items of the patient information, and so on until one or more matching clinical trials are identified.

The patient recruitment module 154 can be configured to report the identification of the patient as a potential subject for a clinical trial to the one or more prescriber and/or healthcare provider devices 102, service provider computers 104, pharmacy claims processor computers 106, EMR vendor/aggregator systems 115, and/or patient support service centers 110.

The patient recruitment module 154 may be configured to identify, based on matching a patient query data structure with a clinical trial protocol data structure, the patient for participation in the clinical trial.

Returning to FIG. 1, according to an example embodiment, the data files 142 may store healthcare request records associated with communications received from various prescriber/healthcare provider devices 102 (either directly or via the EMR vendor/aggregator system 115) and/or various pharmacy claims processor computers 106. The data files 142 may also store any number of suitable routing tables that facilitate determining the destination of communications received from a prescriber/healthcare provider device 102 and/or a pharmacy claims processor computer 106. In one or more example embodiments, the service provider computer 104 may include or otherwise be in communication with one or more suitable databases and/or data storage devices 112.

Additionally, in certain example embodiments, the prescriber/healthcare provider devices 102, the service provider computer 104, the pharmacy claims processor computer 106, the pharmacy computers 108, the patient support service computer 110, and/or the EMR vendor/aggregator system 115 may be in communication with one or more data storage devices, such as database 112. The database 112 may receive, store, and provide, as needed, healthcare requests data from the service provider computer 104. In certain example embodiments, the healthcare requests data includes all or any portion of the data included in electronic healthcare requests received by the service provider computer 104 from a prescriber/healthcare provider computer 102 (either directly or via an EMR vendor/aggregator system 115) and/or electronic healthcare responses to the electronic healthcare requests received from a pharmacy claims processor computer 106 or prior authorization clearinghouse. In addition, the database 112 or another database may include business rules providing methodologies for comparing and evaluating electronic healthcare requests and associated responses by the service provider computer 104. The database 112 can also include a schedule table or listing of records for prescribers, vendors, aggregators, claims processors, and/or prior authorization clearinghouses that receive the prior authorization evaluation services. In addition, the database 112 can include a table, schedule, or listing of records for medications that have financial assistance programs and/or those medications that may include additional messaging for the patient (e.g., REMS program messaging or other patient or medication specific messaging) and the associated messaging to be included in the electronic prior authorization response. The database 112 can also include a listing of minimum data requirements for processing each form of electronic prior authorization request, a listing of one or more data fields for each form of electronic prior authorization request and the associated expected data format for data in each of those data fields, and one or more conversion tables for converting data that is in an incorrect format into a correct format. The database can also include patient information (e.g., patient identifiers (e.g., patient social security number, a subset of the patient social security number, health insurance claim number (HICN), cardholder ID, etc.), patient name, patient gender, patient date of birth, patient address, patient zip code), benefits provider identifiers (e.g., Banking Identification Number (BIN Number), BIN Number and Processor Control Number (PCN), or BIN Number and Group ID), benefits provider name, date of service, software and/or vendor certification identification, pharmacy identification qualifier, pharmacy identification (e.g., National Provider Identifier (NPI) code, Drug Enforcement Administration (DEA) number, state license number, NCPDP Provider ID, store and/or chain name, store address, or the like), product/service information (identifier) (e.g., medication/product/service name(s), National Drug Code (NDC) code, RxNorm medication identifiers, days' supply, quantity dispensed, and the like), patient history information including, but not limited to, medication history information (e.g., total number of medications/products/services, medication/product/service name(s), NDC codes, RxNorm medication identifiers, quantity of medication to be dispensed), prescriber identification number (i.e., prescriber ID ((e.g., NPI code, DEA number), prescriber name, and prescriber zip code or other postal zone identifier for a prescription. Alternatively, the data storage function may be included in the service provider computer 104 itself, such as in the memory 136 of the service provider computer 104.

The database 112 can also include clinical trial data. Clinical trial data may include criteria associated with one or more clinical trials. Clinical trial data may include one or more clinical trial protocol data structures as described herein. The database 112 can also include patient information. Patient information may comprise one or more patient query data structures as described herein.

The service provider computer 104 may include additional program modules for performing other processing methods described herein. Those of ordinary skill in the art will appreciate that the service provider computer 104 may include alternate and/or additional components, hardware, or software without departing from the scope of the disclosure. For example, the service provider computer 104 may include additional program modules such as an Internet browser or other software for interacting with the prescriber/healthcare provider device 102 (either directly or via the EMR vendor/aggregator system 115), and/or the pharmacy claims processor computers 106.

With continued reference to the service provider computer 104, the one or more I/O interfaces 158 may facilitate communication between the service provider computer 104 and one or more input/output devices, for example, one or more user interface devices, such as a display, keypad, mouse, control panel, touch screen display, remote control, microphone, etc., that facilitate user interaction with the service provider computer 104. The one or more network interfaces 160 may facilitate connection of the service provider computer 104 to one or more suitable networks, for example, the network 114 illustrated in FIG. 1. In this regard, the service provider computer 104 may communicate with other components of the system 100.

With continued reference to FIG. 1, any number of pharmacy claims processor computers 106 or prior authorization clearinghouses (referred to hereinafter as "pharmacy claims processor computer(s) 106") may be associated with any number of pharmacy claims processors (e.g., pharmacy benefits manager (PBM), insurance provider, government insurance provider (e.g., Medicare, Medicaid) or a prior authorization clearinghouse. Each pharmacy claims processor computer 106 may be any suitable processor-driven devices, such as, but not limited to, a server computer, a personal computer, a laptop computer, a handheld computer, and the like. In addition to having one or more processors 162, the pharmacy claims processor computer 106 may further include one or more memories 164, one or more input/output (I/O) interfaces 166, and one or more network interfaces 168. The memory 164 may store data files 170 and various program modules, such as an operating system (OS) 172 and a benefits management module 174. The benefits management module 174 may be operable to access one or more databases in database 112 or in another database communicably coupled to the pharmacy claims processor computer 106. In one example, the pharmacy claims processor computer 106 may have a dedicated connection to the database 112. However, the pharmacy claims processor computer 106 may also communicate with the database 112 via the network 114 shown, or via another network. The I/O interface(s) 166 may facilitate communication between the processors 162 and various I/O devices, such as a keyboard, mouse, printer, microphone, speaker, monitor, bar code reader/scanner, RFID reader, and the like. The network interface(s) 170 each may take any of a number of forms, such as a network interface card, a modem, a wireless network card, and the like.

Generally, the pharmacy claims processor computer 106, via the benefits management module 174, may facilitate the determination/processing of healthcare requests including electronic prior authorization requests (e.g., an electronic prior authorization initiation request, an electronic prior authorization request, an electronic prior authorization appeal request, and/or an electronic prior authorization cancel request formatted according to the NCPDP Script Standard). According to various example embodiments, the pharmacy claims processor computer 106 may be associated with, without limitation, a PBM, an insurance company, a government healthcare provider, another third-party payor, a prior authorization clearinghouse, or a pharmacy claims processor processing electronic prior authorization requests on behalf of one or more third-party payors and/or healthcare providers.

The pharmacy claims processor computer 106 include additional program modules for performing other processing methods described herein. Those of ordinary skill in the art will appreciate that the pharmacy claims processor computer 106 may include alternate and/or additional components, hardware, or software without departing from the scope of the disclosure. For example, the pharmacy claims processor computer 106 may include additional program modules such as an Internet browser or other software for interacting with the service provider computer 104.

With continued reference to FIG. 1, any number of pharmacy computers 108 may be associated with any number of pharmacies and/or pharmacists. Each pharmacy computer 108 may be any suitable processor-driven device that facilitates receiving, processing, and/or fulfilling prescription requests and/or prescription responses received from the service provider computer 104. For example, a pharmacy computer 108 may be a processor-driven device associated with (e.g., located within) a pharmacy. As desired, the pharmacy computer 108 may include any number of special-purpose computers or other particular machines, application-specific integrated circuits, microcontrollers, personal computers, minicomputers, mainframe computers, servers, and the like. In certain example embodiments, the operations of the pharmacy computer 108 may be controlled by computer-executed or computer-implemented instructions that are executed by one or more processors associated with the pharmacy computer 108 to form a special-purpose computer or other particular machine that is operable to facilitate the receipt, processing, and/or fulfillment of prescription requests (e.g., a prescription claim request, a billing request, pharmacy billing request, or predetermination of benefits request) received from the service provider computer 104. The one or more processors that control the operations of a pharmacy computer 108 may be incorporated into the pharmacy computer 108 and/or may be in communication with the pharmacy computer 108 via one or more suitable networks. In certain example embodiments, the operations and/or control of the pharmacy computer 108 may be distributed among several processing components.

Similar to other components of the system 100, each pharmacy computer 108 may include one or more processors 176, one or more memory devices 178, one or more I/O interfaces 180, and one or more network interfaces 182. The one or more memory devices 178 may be any suitable memory devices, for example, caches, read-only memory device, random access memory devices, magnetic storage devices, removable memory devices, etc. The one or more memory devices 178 may store data, executable instructions, and/or various program modules utilized by the pharmacy computer 108, for example, data files 184, an OS 186, and a pharmacy management module 188. The data files 184 may include any suitable information that is utilized by the pharmacy computer 108. The OS 186 may be a suitable software module that controls the general operation of the pharmacy computer 108. The OS 186 may also facilitate the execution of other software modules by the one or more processors 176. The OS 186 may be any operating system known in the art or which may be developed in the future including, but not limited to, Microsoft Windows®, Apple OSX™ Linux, Unix, Apple iOS™, Google Android™, or a mainframe operating system.

The one or more I/O interfaces 180 may facilitate communication between the pharmacy computer 108 and one or more input/output devices, for example, one or more user interface devices, such as a display, keypad, control panel, touch screen display, remote control, microphone, etc., that facilitate user interaction with the pharmacy computer 108. The one or more network interfaces 182 may facilitate connection of the pharmacy computer 108 to one or more suitable networks, for example, the network 114 illustrated in FIG. 1. In this regard, the pharmacy 108 may receive prescription responses and/or other communications from the service provider computer 104 and the pharmacy computer 108 may communicate information associated with processing prescription requests to the service provider computer 104.

The pharmacy management module 188 may be a software application(s), including a dedicated program, for fulfilling healthcare transaction orders, reading and/or updating medical records (e.g., prescription records), facilitating patient billing, etc., as well as interacting with the service provider computer 104. For example, a pharmacist or other pharmacy employee, may utilize the pharmacy management module 188 in filling a prescription, recording and/or updating a patient's medical prescription history, billing a patient, and preparing and providing a prescription request for information to the service provider computer 104. Furthermore, the pharmacy computer 108 may utilize the pharmacy management module 188 to retrieve or otherwise receive data, messages, or responses from the healthcare provider device 102 and/or other components of the system 100.

With continued reference to FIG. 1, any number of patient support center computers 110 (also referred to as "Hubs") may be associated with any number of pharmaceutical companies. Each patient support center computer 110 may be any suitable processor-driven devices, such as, but not limited to, a server computer, a personal computer, a laptop computer, a handheld computer, and the like. In addition to having one or more processors, the patient support center computer 110 may further include one or more memories, one or more input/output (I/O) interfaces, and one or more network interfaces. The memory may store data files and various program modules, such as an operating system (OS) and a management module. The management module may be operable to access one or more databases in database 112 or in another database communicably coupled to the patient support center computer 110. In one example, the patient support center computer 110 may have a dedicated connection to the database 112. However, the patient support center computer 110 may also communicate with the database 112 via the network 114 shown, or via another network. The I/O interface(s) may facilitate communication between the processors and various I/O devices, such as a keyboard, mouse, printer, microphone, speaker, monitor, bar code reader/ scanner, RFID reader, and the like. The network interface(s) each may take any of a number of forms, such as a network interface card, a modem, a wireless network card, and the like.

Generally, the patient support center computer 110, via the management module, may be configured to provide a variety of services to patients, including helping with insurance benefit verification, contacting pharmacy benefit managers to urge prior authorization, arranging for delivery of drugs (some must remain refrigerated), and following up with the patient to monitor their dosing regimen.

The patient support center computer 110 may include additional program modules for performing other processing methods described herein. Those of ordinary skill in the art will appreciate that the patient support center computer 110 may include alternate and/or additional components, hardware, or software without departing from the scope of the disclosure. For example, the patient support center computer 110 may include additional program modules such as an Internet browser or other software for interacting with the prescriber and/or healthcare provider device 102 and/or the service provider computer 104.

Generally, network devices and systems, including one or more prescriber and/or healthcare system devices 102, service provider computers 104, pharmacy claims processor computers 106, pharmacy computers 108, patient support service computers 110, and/or EMR vendor/aggregator systems 115 may include or otherwise be associated with suitable hardware and/or software for transmitting and receiving data and/or computer-executable instructions over one or more communication links or networks. These network devices and systems may also include any number of processors for processing data and executing computer-executable instructions, as well as other internal and peripheral components currently known in the art or which may be developed in the future. Further, these network devices and systems may include or be in communication with any number of suitable memory devices operable to store data and/or computer-executable instructions. By executing computer-executable instructions, each of the network devices may form a special-purpose computer or particular machine.

The network 114 may include any telecommunication and/or data network, whether public, private, or a combination thereof, including a local area network, a wide area network, an intranet, the Internet, intermediate handheld data transfer devices, and/or any combination thereof and may be wired and/or wireless, or any combination thereof. The network 114 may also allow for real time, offline, and/or batch transactions to be transmitted between or among the one or more prescriber and/or healthcare system devices 102, service provider computers 104, pharmacy claims processor computers 106, pharmacy computers 108, patient support service computers 110, and/or EMR vendor/aggregator systems 115. Various methodologies as described herein, may be practiced in the context of distributed computing environments. Although the service provider computer 104 is shown for simplicity as being in communication with the prescriber/healthcare provider device 102 (either directly or indirectly via the EMR vendor/aggregator system 115) or the pharmacy claims processor computer 106 via one intervening network 114, it is to be understood that any other network configurations are possible. For example, intervening network 114 may include a plurality of networks, each with devices such as gateways and routers for providing connectivity between or among the components of the system 100. Instead of or in addition to the network 114, dedicated communication links may be used to connect various devices in accordance with an example embodiment. For example, the service provider computer 104 may form the basis of network 114 that interconnects the prescriber/ healthcare provider device 102 (either directly or indirectly via the EMR vendor/aggregator system 115), the service provider computer 104, the pharmacy claims processor computer 106, and/or the pharmacy computer 108.

Those of ordinary skill in the art will appreciate that the system 100 shown in and described with respect to FIG. 1 is provided by way of example only. Numerous other operating environments, system architectures, and device and network configurations are possible. Other system embodiments can include fewer or greater numbers of components and may incorporate some or all of the functionality described with respect to the system components shown in FIG. 1. For example, the service provider computer 104 is implemented as a specialized processing machine that includes hardware and/or software for performing the methods described herein. Accordingly, the exemplary embodiments described herein should not be construed as being limited to any particular operating environment, system architecture, or device configuration.

Figure 3:
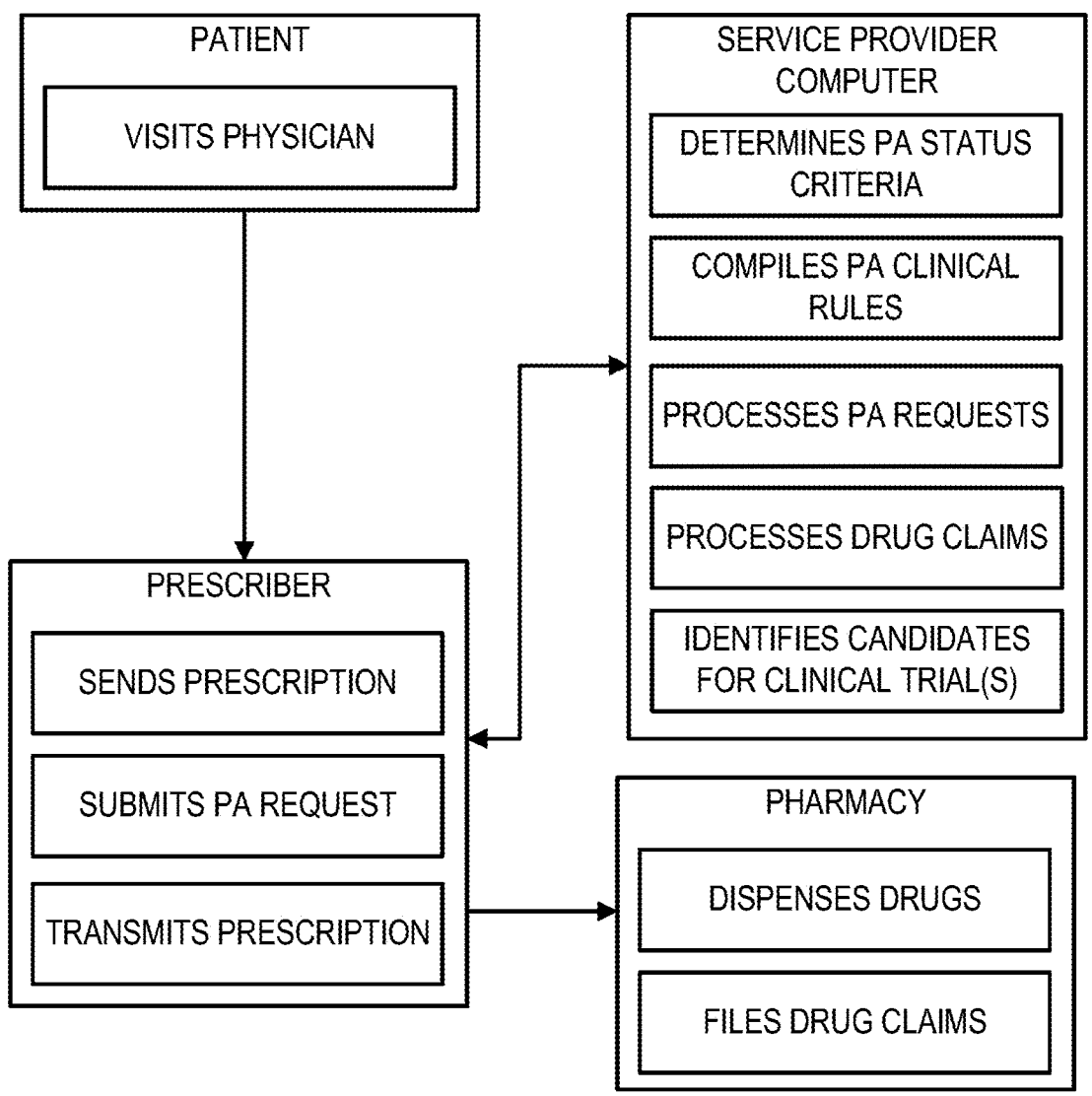
FIG. 3 illustrates an example method.

FIG. 3 is a block diagram that schematically illustrates an example of a combined health care request and clinical trial recruitment process that may occur during an interaction between a patient and a healthcare provider. In the example of FIG. 3, the healthcare request comprises an electronic prior authorization (ePA) process for obtaining real-time (or near real-time) approval of an ePA and identifying a patient as a candidate for a clinical trial. The example ePA process can utilize patient-specific and drug-specific PA criteria (e.g., as established by the service provider). The example ePA process shown in FIG. 3 involves a multi-part transaction that enables patient-specific and drug-specific PA criteria and a real-time approval process. In this example, a patient visits a prescriber (e.g., the patient's physician) who prescribes a medication and electronically transmits a prescription request (ePrescription) to a pharmacy and an ePA to a service provider (such as a payer, the patient's health insurer, or other service provider). The pharmacy can dispense the prescribed medication to the patient and file a medication reimbursement claim. The service provider may process the ePA and drug claims requests and establish the criteria and clinical rules for the PA process for the prescription medication. The service provider may also process patient information associated with the ePA to determine if the patient is a candidate for participation in one or more clinical trials. The prescriber and the service provider may exchange questions (from the service provider, based on the PA criteria and clinical rules) and answers (from the prescriber, based on the medical history of the patient) until a decision by the service provider is made on whether to approve or reject the PA request for the prescribed medication. The prescriber and the service provider may also exchange questions in order to identify the patient as a candidate for the clinical trial. As will be further discussed below, service providers may require information on patient adherence to a treatment regimen before the PA request for a medication can be approved or before the patient may be identified as a candidate for a clinical trial. In such cases, patient adherence data (e.g., laboratory test results) may be used to determine a likelihood that the patient is indeed adhering to the treatment regimen, and this likelihood may be factored into the PA and clinical trial approval process.

Electronic prior authorization platforms can make the ePA request form accessible from within a user account associated with the prescribing physician. For example, the prescribing physician may access the PA platform via a network (such as the Internet) using a graphical user interface (e.g., a web browser or dedicated application).

A prescribing physician or other authorized party affiliated with the physician (e.g., the physician's office staff, clinical research coordinator, and the like) will generally be hereinafter referred to generically as the "prescriber" for the sake of brevity. The term medication includes drugs, medicines, pharmaceuticals, medicaments, medicinal products, medical devices or appliances, or any other substance, device, or apparatus having properties for treating or preventing disease in humans or animals.

An ePA system (such as, e.g., any of the systems described herein, including embodiments of the system 100 described with reference to FIG. 1) can include functionality for speeding up both the clinical trial recruitment process and the ePA determination process by reducing the back-and-forth between the prescriber and service provider described above. The ePA system can provide a workflow process that accesses locally stored data on a service provider's PA criteria and PA rules in order to provide the relevant PA and clinical trial questions to the prescriber, accept the prescriber's responses, prepare and submit the appropriate ePA form to the service provider and/or further the clinical trial enrollment process. Since the ePA is likely to include answers to the questions the service provider needs to accept the ePA request, the ePA can in many cases be processed in (near) real-time so that the prescriber can promptly receive a decision on the request.

The following is a non-limiting, illustrative example of the workflow that the ePA system can establish with the prescriber. The prescriber initiates an ePA on the ePA system by, for example, accessing a user interface (UI) on a computing device (e.g., an application which allows the prescriber computing device to communicate with the ePA system). In an embodiment, the prescriber can select a button on the UI (e.g., "Send to Plan") to submit the at least partially completed ePA for processing. As will be discussed, the destination where the ePA is transmitted for processing will depend on the system configuration. The prescriber may send a message asking the service provider "What are my questions?"—e.g., what information does the service provider want to know from the prescriber in order to determine whether the service provider should approve the PA request and remit payment?

The UI on the prescriber computing device can be associated with the prescriber's electronic medical record system or e-prescription system. In some cases, the UI is provided by the ePA system (e.g., as a web application). The UI may implement the NCPDP ePA standard for increased compatibility with ePA systems, which also implement the NCPDP standard. The prescriber can have an authenticated account on the ePA system.

The ePA is transmitted by the ePA system to the service provider for the service provider to process. The service provider may communicate a list of questions appropriate for the patient's insurance plan, prescribed medication, and potential for participation in one or more clinical trials. The prescriber can respond by submitting answers to the questions to the service provider via the UI. As discussed above, this can lead to a back-and-forth between the prescriber and the service provider as the service provider's questions are answered by the prescriber, ultimately resulting in either approval or denial of the ePA and identification (or not) of the patient as a candidate in a clinical trial.

Figure 4:
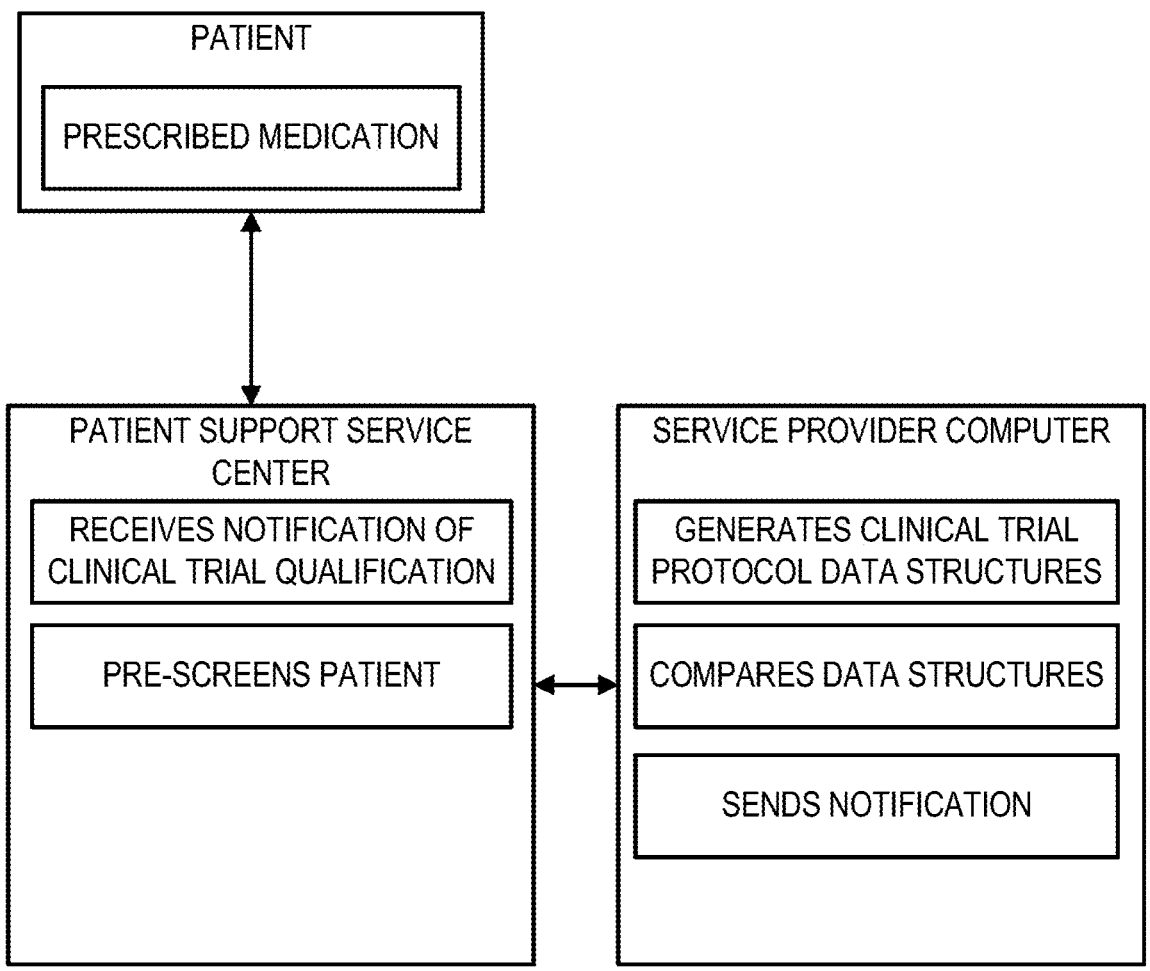
FIG. 4 illustrates an example method.

FIG. 4 is a block diagram that schematically illustrates an example of a clinical trial recruitment process that may occur during an interaction between a patient and a patient support service center (or hub). Pharmaceutical companies have established specialty programs called patient support service centers or "hubs," which are customer service organizations typically centered around a single specialty medication (e.g., a drug with a limited number of patients often an oncology drug). The hub provides a variety of services to patients, including helping with insurance benefit verification, contacting pharmacy benefit managers to urge prior authorization, arranging for delivery of drugs (some must remain refrigerated), and following up with the patient to monitor their dosing regimen. A patient may be enrolled into a hub program in a variety of ways. For example, a prescriber can search for, fill out, and submit a hub enrollment for a patient at the time of prescribing a medication and/or a system can automatically detect that a hub program is affiliated with a medication being prescribed to a patient by a prescriber and recommend the hub to the prescriber and/or the patient. In any event, once the patient is prescribed a mediation and is participating in a hub, the hub may receive a notification that the patient has been identified as a candidate for participation in a clinical trial. For example, a patient support service center may receive such a notification from a service provider computer. The service provider computer may maintain patient data and compare the patient data to clinical trial data/clinical trial protocol data to determine that the patient is a candidate for a clinical trial. The service provider computer may have previously generated a patient search query data structure and compare the patient search query data structure to one or more clinical trial data structures. For example, as new clinical trials are created, new clinical trial data structures are generated and may be compared to all current patient search query data structures to identify candidates for participation in the clinical trial. Once the service provider computer determines that the patient is a candidate for participation in the clinical trial, the service provider computer may send a notification to the patient support service center computer. The patient support service center computer may initiate communication with the patient via, for example, a patient computing device. The patient support service center computer may communicate with the patient in order to pre-screen the patient to ensure that the patient meets the criteria of the clinical trial and coordinate enrollment into the clinical trial.

Figure 5:
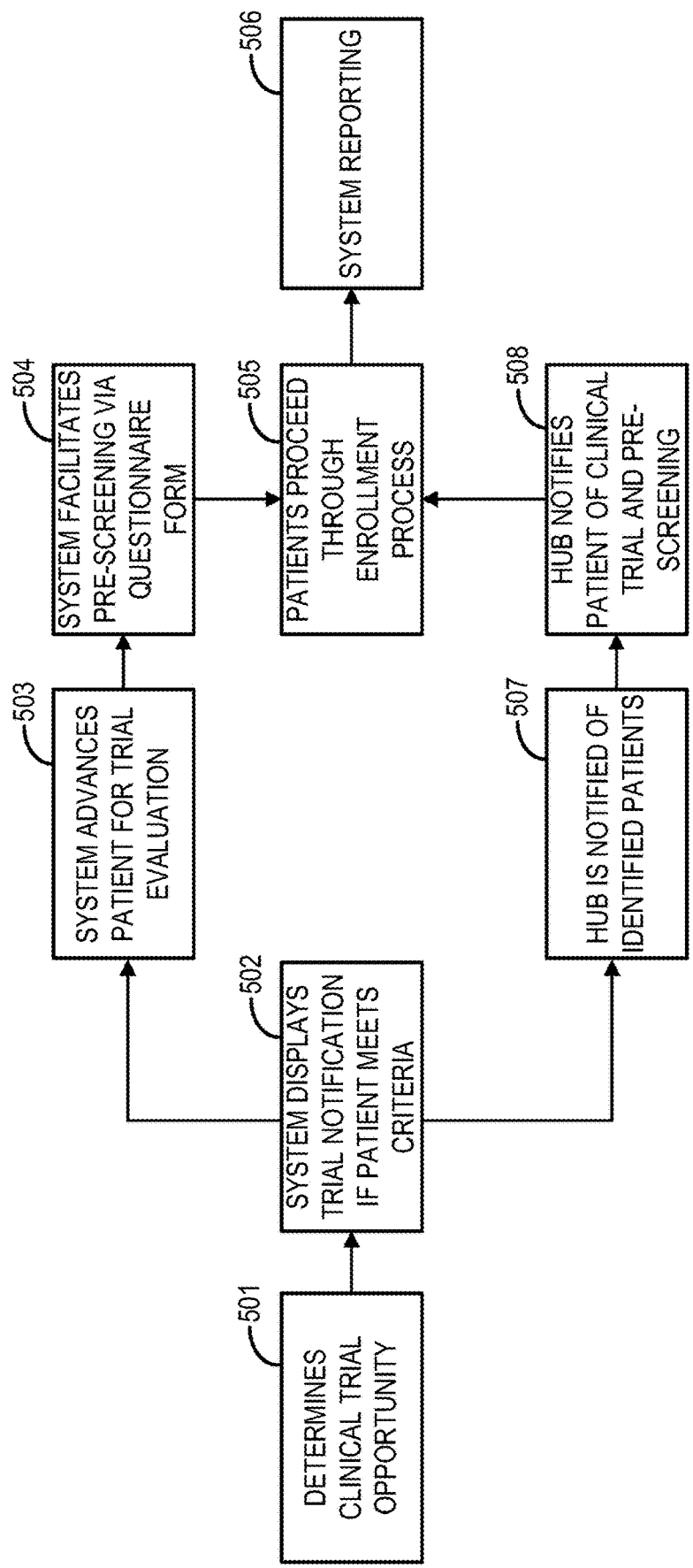
FIG. 5 illustrates an example method.

FIG. 5 is a block diagram that schematically illustrates an example of a clinical trial recruitment process that may occur either during an interaction between a patient and a healthcare provider or between a patient and a patient support service center (or hub). At block 501, during a healthcare request process, a service provider computer determines a clinical trial opportunity using patient data and clinical trial data. The clinical trial opportunity may be determined by comparing patient data to identification criteria that may be determined based on clinical trial protocols, and may include, for example, demographic information, prescribed medication information, and diagnosis information with variability based on available data. At block 502, if the patient meets identification criteria, a clinical trial notification may be sent. The clinical trial notification may be sent to the healthcare provider (e.g., a physician, a research coordinator, and the like). The clinical trial notification may be sent to the patient (e.g., via a direct communication with the patient using a software application and/or messaging). The clinical trial notification may be sent to a patient support service center (e.g., a hub).

Figure 6:
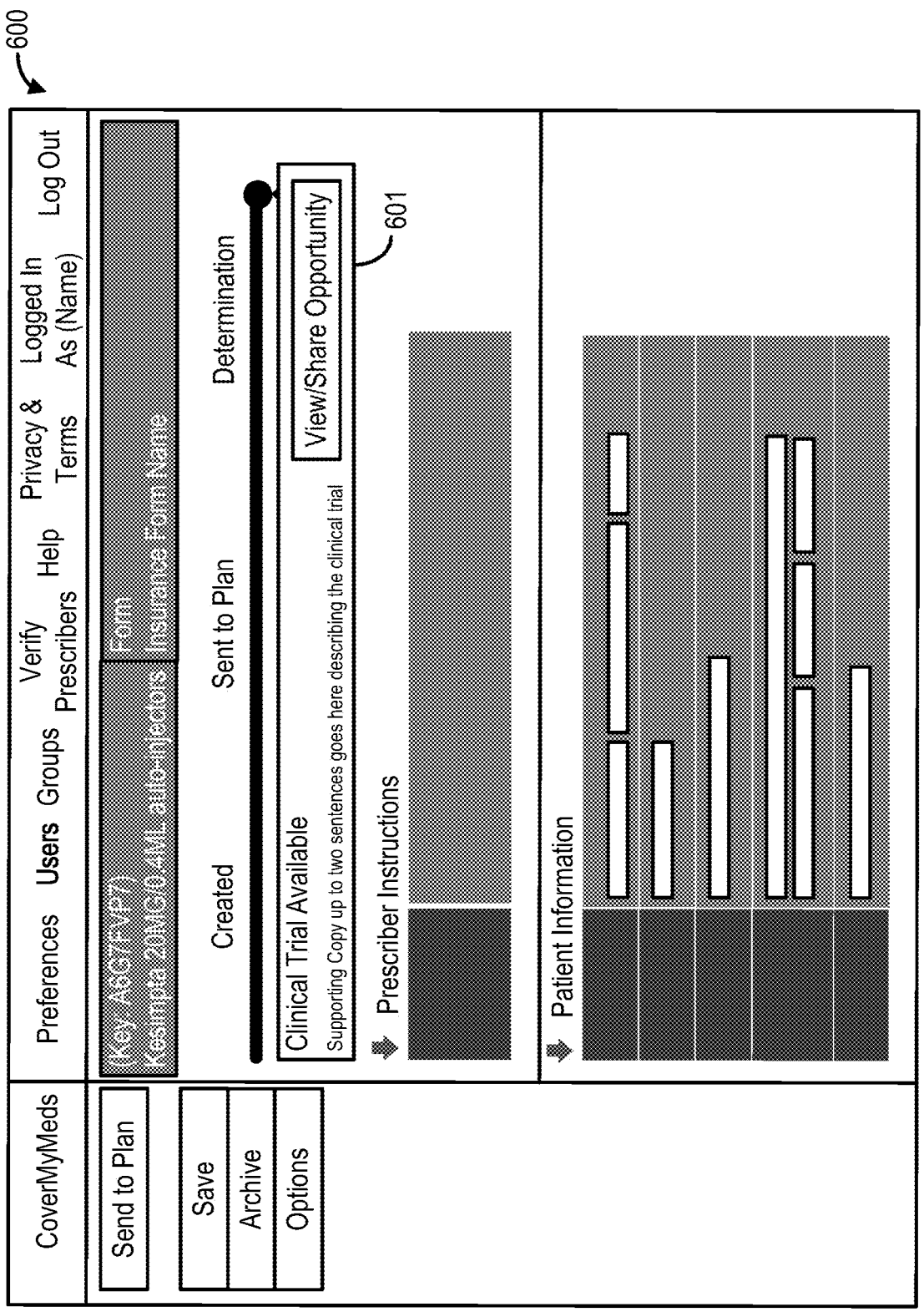
FIG. 6 illustrates an example user interface.

An example display is shown in FIG. 6 for an embodiment where the clinical trial notification is sent to the healthcare provider. As shown in FIG. 6, a clinical trial notification 601 may be displayed on a user interface 600. The healthcare provider may engage the clinical trial notification 601 to view additional information on the clinical trial and to discuss with the patient accordingly. The healthcare provider may engage the clinical trial notification 601 to share the clinical trial opportunity with another party, for example, with the patient, with another party at the healthcare provider (e.g., research coordinator), or another healthcare provider. The healthcare provider may assesses the patient's applicability for the clinical trial. If the patient wishes to participate, the healthcare provider may use the user interface 600 to advance the patient for pre-screening at block 503. A notification may be sent to a research investigator associated with the clinical trial, including patient information and any other additional information as may be necessary. One or more questionnaires or surveys may be generated and provided to the healthcare provider and/or the patient at block 504 to facilitate pre-screening of the patient for the clinical trial.

Figure 9:
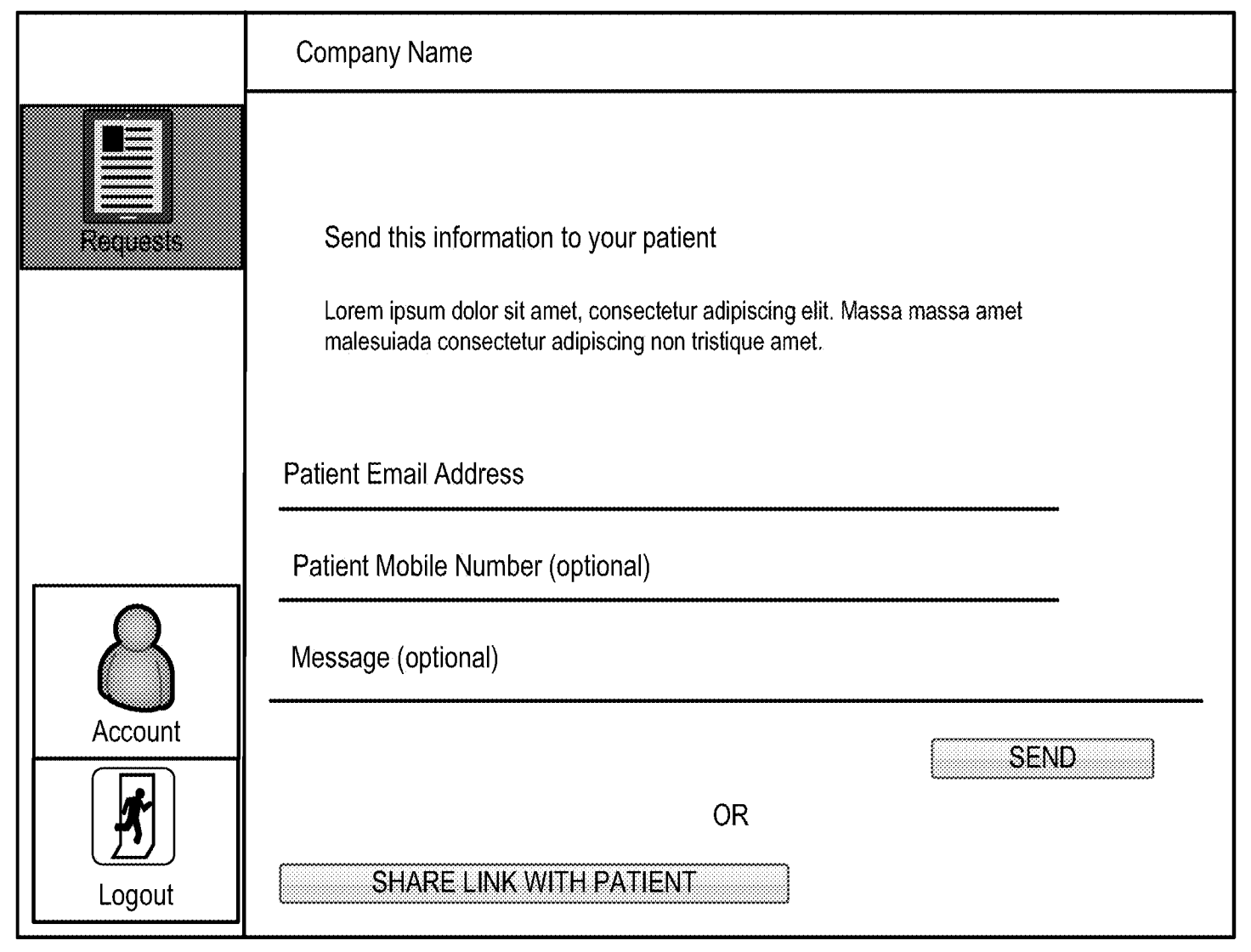

As shown in FIG. 7 and FIG. 8, a user interface 700 and a user interface 800 may be presented to assist the healthcare provider and/or the patient in performing the pre-screening process, culminating in a determination, shown in FIG. 9, that the patient is, or is not, a candidate for the clinical trial. Returning to FIG. 5, at block 505, successfully pre-screened patients may be referred to the clinical trial site for final screening and enrollment into the clinical trial. Patient information may be maintained for screening failure analysis.

In an embodiment, in the event the patient recruitment process is not pursued during the interaction between the healthcare provider and the patient, a patient support service center (hub) may be notified that a patient meets identification criteria for a clinical trial at block 507. At block 508, via a patient outreach function, the patient support service center may contact the patient and pre-screen the patient for the clinical trial. If the patient wishes to participate, at block 505, successfully pre-screened patients may be referred to the clinical trial site for final screening and enrollment into the clinical trial. Patient information may be maintained for screening failure analysis.

At block 506, the system may generate one or more reports related to patients that were successfully pre-screened, patients that were not successfully pre-screened, and the like.

Figure 10:
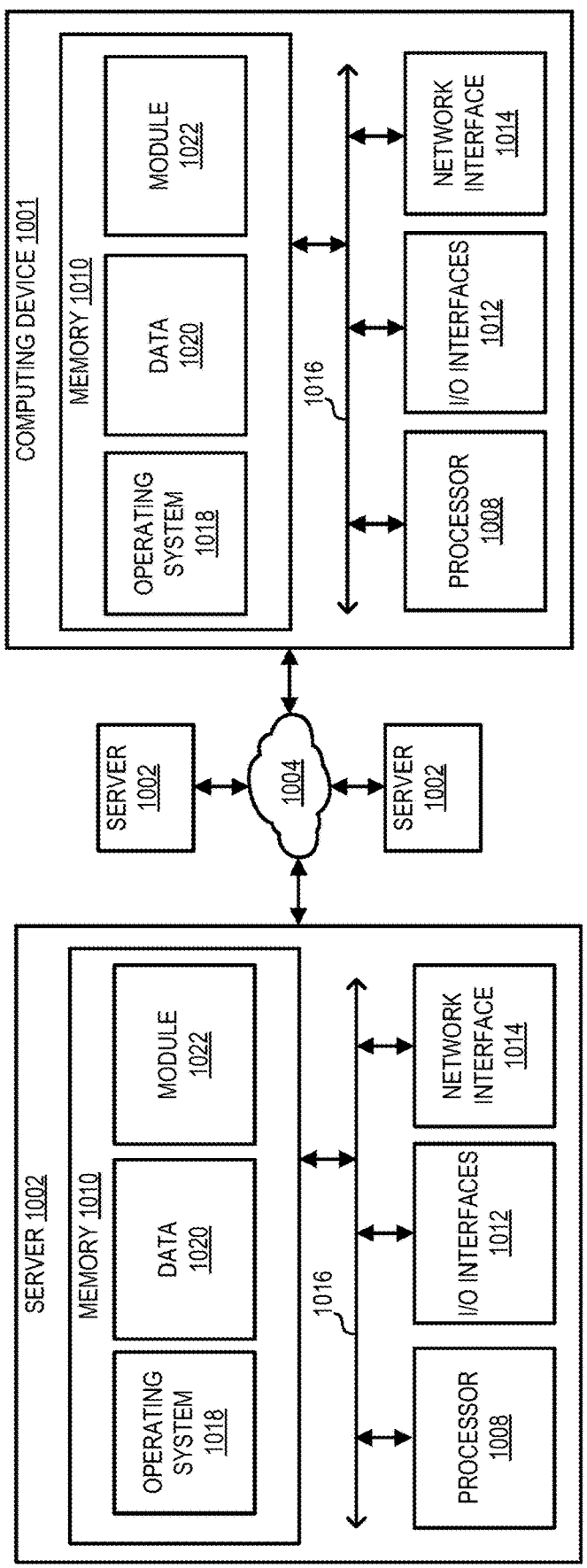
FIG. 10 illustrates an example computing device.

FIG. 10 is a block diagram depicting an environment 1000 comprising non-limiting examples of a computing device 1001 and a server 1002 connected through a network 1004. In an aspect, some or all steps of any described method may be performed on a computing device as described herein. In varying embodiment, the computing device 1001 and/or the server 1002 may be one or more of the healthcare provider device 102, the service provider computer 104, the pharmacy claims processing computer 106, the pharmacy computer 108, the EMR vendor/aggregator 115, the database 112, and/or the patient support service center 110.

The computing device 1001 can comprise one or multiple computers configured to store one or more of data 1020, one or more modules 1022, and the like. The server 1002 can comprise one or multiple computers configured to store one or more of data 1020, one or more modules 1022, and the like. Multiple servers 1002 can communicate with the computing device 1001 via the through the network 1004.

The data 1020 may comprise any and/or all of the data stored as described with regard to the database 112. For example, the data 1020 may comprise one or more of, patient data, clinical trial data, patient query data structures, clinical trial protocol data structures, prior authorization data, and the like.

The one or more modules 1022 may comprise one or more modules as described here including for example, one or more of the EMR module 128, the healthcare request module 132, the patient recruitment module 154, the healthcare request processing module 156, the benefits management module 174, the pharmacy management module 188, and the like.

The computing device 1001 and the server 1002 can be a digital computer that, in terms of hardware architecture, generally includes a processor 1008, memory system 1010, input/output (I/O) interfaces 1012, and network interfaces 1014. These components (1008, 1010, 1012, and 1014) are communicatively coupled via a local interface 1016. The local interface 1016 can be, for example, but not limited to, one or more buses or other wired or wireless connections, as is known in the art. The local interface 1016 can have additional elements, which are omitted for simplicity, such as controllers, buffers (caches), drivers, repeaters, and receivers, to enable communications. Further, the local interface may include address, control, and/or data connections to enable appropriate communications among the aforementioned components.

The processor 1008 can be a hardware device for executing software, particularly that stored in memory system 1010. The processor 1008 can be any custom made or commercially available processor, a central processing unit (CPU), an auxiliary processor among several processors associated with the computing device 1001 and the server 1002, a semiconductor-based microprocessor (in the form of a microchip or chip set), or generally any device for executing software instructions. When the computing device 1001 and/or the server 1002 is in operation, the processor 1008 can be configured to execute software stored within the memory system 1010, to communicate data to and from the memory system 1010, and to generally control operations of the computing device 1001 and the server 1002 pursuant to the software.

The I/O interfaces 1012 can be used to receive user input from, and/or for providing system output to, one or more devices or components. User input can be provided via, for example, a keyboard and/or a mouse. System output can be provided via a display device and a printer (not shown). I/O interfaces 1012 can include, for example, a serial port, a parallel port, a Small Computer System Interface (SCSI), an infrared (IR) interface, a radio frequency (RF) interface, and/or a universal serial bus (USB) interface.

The network interface 1014 can be used to transmit and receive from the computing device 1001 and/or the server 1002 on the network 1004. The network interface 1014 may include, for example, a 10BaseT Ethernet Adaptor, a 100BaseT Ethernet Adaptor, a LAN PHY Ethernet Adaptor, a Token Ring Adaptor, a wireless network adapter (e.g., WiFi, cellular, satellite), or any other suitable network interface device. The network interface 1014 may include address, control, and/or data connections to enable appropriate communications on the network 1004.

The memory system 1010 can include any one or combination of volatile memory elements (e.g., random access memory (RAM, such as DRAM, SRAM, SDRAM, etc.)) and nonvolatile memory elements (e.g., ROM, hard drive, tape, CDROM, DVDROM, etc.). Moreover, the memory system 1010 may incorporate electronic, magnetic, optical, and/or other types of storage media. Note that the memory system 1010 can have a distributed architecture, where various components are situated remote from one another, but can be accessed by the processor 1008.

The software in memory system 1010 may include one or more software programs, each of which comprises an ordered listing of executable instructions for implementing logical functions. In the example of FIG. 10, the software in the memory system 1010 of the computing device 1001 can comprise the data 1020, the one or more modules 1022, and a suitable operating system (O/S) 1018. In the example of FIG. 10, the software in the memory system 1010 of the server 1002 can comprise, the data 1020, the one or more modules 1022, and a suitable operating system (O/S) 1018. The operating system 1018 essentially controls the execution of other computer programs and provides scheduling, input-output control, file and data management, memory management, and communication control and related services.

For purposes of illustration, application programs and other executable program components such as the operating system 1018 are illustrated herein as discrete blocks, although it is recognized that such programs and components can reside at various times in different storage components of the computing device 1001 and/or the server 1002. An implementation of the one or more modules 1022 can be stored on or transmitted across some form of computer readable media. Any of the disclosed methods can be performed by computer readable instructions embodied on computer readable media. Computer readable media can be any available media that can be accessed by a computer. By way of example and not meant to be limiting, computer readable media can comprise "computer storage media" and "communications media." "Computer storage media" can comprise volatile and non-volatile, removable and non-removable media implemented in any methods or technology for storage of information such as computer readable instructions, data structures, program modules, or other data. Exemplary computer storage media can comprise RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computer.

Figure 11:
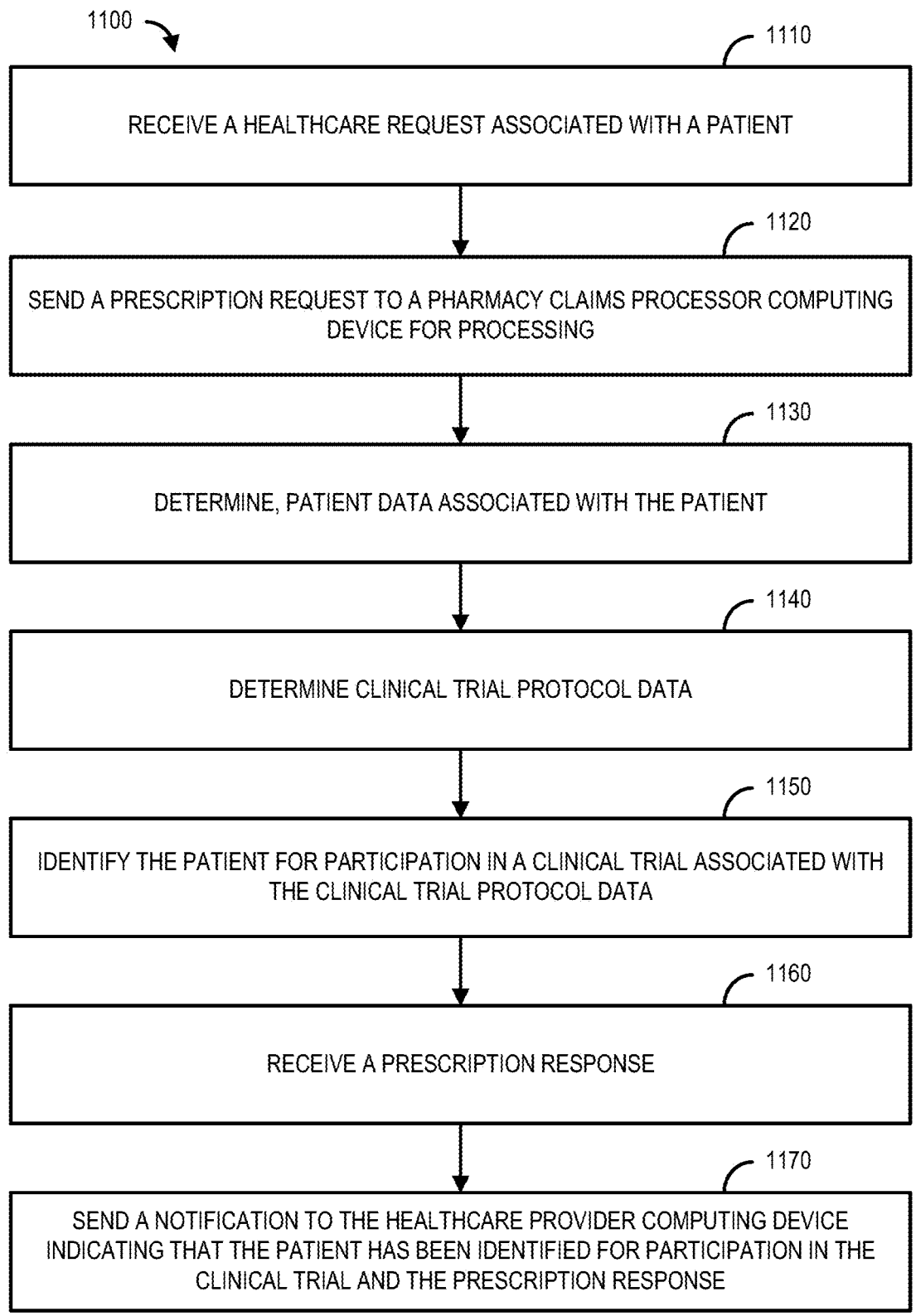
FIG. 11 illustrates an example method.

In an embodiment, one or more of the EMR module 128, the healthcare request module 132, the patient recruitment module 154, the healthcare request processing module 156, the benefits management module 174, the pharmacy management module 188, alone or in combination or sub-combination, may be configured to perform a method 1100, shown in FIG. 11. The method 1100 may be performed in whole or in part by a single computing device or a plurality of computing devices. For example, the method 1100 may be performed in whole or in part by one or more of the healthcare provider device 102, the service provider computer 104, the pharmacy claims processing computer 106, the pharmacy computer 108, the EMR vendor/aggregator 115, the database 112, the patient support service center 110, alone, or in combination or sub-combination. At 1110, a healthcare request associated with a patient may be received. The healthcare request may be received by a service provider computing device, a pharmacy claims processing computing device, a pharmacy computing device, an EMR vendor/aggregator computing device, and the like. The healthcare request may be received from a healthcare provider computing device associated with a prescriber. The healthcare request may comprise a prior authorization request or a prescription benefit check request.

The method 1100 may comprise sending, based on the healthcare request, a prescription request to a pharmacy claims processor computing device for processing at 1120. The pharmacy claims processor computing device may process the healthcare request as described herein. For example, the pharmacy claims processor computing device may approve or deny a prior authorization request.

The method 1100 may comprise determining, based on the healthcare request, patient data associated with the patient at 1130. Determining, based on the healthcare request, the patient data associated with the patient may comprise at least one of: extracting the patient data from the healthcare request or retrieving the patient data from an electronic health record using an identifier in the healthcare request. The patient data may comprise at least one of: a patient identifier, a patient name, a patient sex, a patient condition, a patient age, a patient weight, a patient height, a patient race, a patient location, a medication specified by the healthcare request, a medication indicated in an electronic health record associated with the patient.

The method 1100 may comprise determining, based on the patient data and clinical trial protocol data, a clinical trial for which the patient may be a candidate at 1140. Determining, based on the patient data and clinical trial protocol data, a clinical trial for which the patient may be a candidate may comprise identifying a clinical trial having clinical trial protocol data that matches the patient data. The method 1100 may further comprise determining, for a plurality of values of the patient data, an encoding rule or a formatting rule, selectively encoding, based on the encoding rule, a first portion of the plurality of values as encoded data values, selectively formatting, based on the formatting rule, a second portion of the plurality of values as formatted data values, and combining, based on a structure rule, the encoded data values and the formatted data values to generate a patient query data structure. The encoding rule may specify how to express a value as a regular expression based on a data value type. The formatting rule may specify how to express a value as a value based on a data value type. The structure rule may specify an order in which encoded data values and formatted data values should be concatenated. Determining, based on the patient data and clinical trial protocol data, a clinical trial for which the patient may be a candidate may comprise comparing the patient query data structure to one or more clinical trial protocol data structures and based on the comparison, identifying the clinical trial associated with a match between the patient query data structure and the one or more clinical trial protocol data structures.

The method 1100 may comprise identifying, based on the patient data and the clinical trial protocol data, the patient for participation in a clinical trial associated with the clinical trial protocol data at 1150. Identifying, based on the patient data and the clinical trial protocol data, the patient for participation in a clinical trial associated with the clinical trial protocol data may be based on a match between the patient data and the clinical trial protocol data. Identifying, based on the patient data and the clinical trial protocol data, the patient for participation in a clinical trial associated with the clinical trial protocol data may comprise configuring a questionnaire or survey.

The method 1100 may comprise receiving, based on the prescription request, from the pharmacy claims processor computing device, a prescription response at 1160. The prescription response may be for example, an approval or a denial.

The method 1100 may comprise sending a notification to the healthcare provider computing device indicating that the patient has been identified for participation in the clinical trial and the prescription response at 1170. Sending the notification to the healthcare provider computing device indicating that the patient has been identified for participation in the clinical trial and the prescription response may cause sending a referral link to a patient computing device and pre-screening the patient for participation in the clinical trial. Sending the notification to the healthcare provider computing device may comprise sending the questionnaire or the survey to the healthcare provider computing device.

In an embodiment, one or more of the EMR module 128, the healthcare request module 132, the healthcare request processing module 156, the patient recruitment module 154, the benefits management module 174, the pharmacy management module 188, alone or in combination or sub-combination, may be configured to perform a method 1200, shown in FIG. 12. The method 1200 may be performed in whole or in part by a single computing device or a plurality of computing devices. For example, the method 1200 may be performed in whole or in part by one or more of the healthcare provider device 102, the service provider computer 104, the pharmacy claims processing computer 106, the pharmacy computer 108, the EMR vendor/aggregator 115, the database 112, the patient support service center 110, alone, or in combination or sub-combination. At 1210, unstructured criteria data expressed as a plurality of values may be received. The method 1200 may comprise determining, for the plurality of values, an encoding rule or a formatting rule at 1220. The encoding rule may specify how to express a value as a regular expression based on a data value type. The formatting rule may specify how to express a value as a value based on a data value type. The structure rule may specify an order in which encoded data values and formatted data values should be concatenated.

The method 1200 may comprise selectively encoding, based on the encoding rule, a first portion of the plurality of values as encoded data values at 1230. The method 1200 may comprise selectively formatting, based on the formatting rule, a second portion of the plurality of values as formatted data values at 1240. The method 1200 may comprise combining, based on a structure rule, the encoded data values and the formatted data values to generate structured criteria data at 1250. The method 1200 may further comprise storing the structured criteria data as a clinical trial protocol data structure and associating the clinical trial protocol data structure with a clinical trial.

The method 1200 may further comprise receiving a patient query data structure associated with a patient, comparing the patient query data structure to the clinical trial protocol data structure, based on a match with every encoded data value and every formatted data value, indicating that the patient query data structure matches the clinical trial protocol data structure, and based on the patient query data structure matching the clinical trial protocol data structure, associating the patient with clinical trial.

Each of constitutional elements described in the present document may consist of one or more components, and names thereof may vary depending on a type of a computing/electronic device. The computing device according to various exemplary embodiments may include at least one of the constitutional elements described in the present document. Some of the constitutional elements may be omitted, or additional other constitutional elements may be further included. Further, some of the constitutional elements of the computing device according to various exemplary embodiments may be combined and constructed as one entity, so as to equally perform functions of corresponding constitutional elements before combination.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

While the methods and systems have been described in connection with preferred embodiments and specific examples, it is not intended that the scope be limited to the particular embodiments set forth, as the embodiments herein are intended in all respects to be illustrative rather than restrictive.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

What is claimed is:

1. A method comprising:
receiving, by at least one healthcare provider computing device, unstructured criteria data associated with a clinical trial, wherein the unstructured criteria data is expressed as a plurality of values, each associated with a data value type;
determining, by the at least one healthcare provider computing device, for the plurality of values, and based on the clinical trial, an encoding rule and a formatting rule;
encoding, by the at least one healthcare provider computing device, based on the encoding rule and the corresponding data value type, a first portion of the plurality of values as encoded data values;
formatting, by the at least one healthcare provider computing device, based on the formatting rule and the corresponding data value type, a second portion of the plurality of values as formatted data values;
concatenating, by the at least one healthcare provider computing device, based on a structure rule associated with the clinical trial, the encoded data values and the formatted data values to generate a clinical trial protocol data structure;
storing, by the at least one healthcare provider computing device, the clinical trial protocol data structure in at least one database, wherein the at least one database is accessible by at least one service provider computing device associated with the at least one healthcare provider computing device;
receiving, by the at least one service provider computing device, a patient query data structure associated with a patient, wherein the patient query data structure is indicative of a plurality of attributes associated with the patient, and wherein the plurality of attributes are: encoded according to the encoding rule associated with the clinical trial and formatted according to the formatting rule associated with the clinical trial;
determining, by the at least one service provider computing device, based on the plurality of attributes and the clinical trial protocol data structure stored in the at least one database, that the patient query data structure matches the clinical trial protocol data structure; and
based on the patient query data structure matching the clinical trial protocol data structure, causing, by the at least one service provider computing device, a notification to be sent to at least a device associated with the patient, wherein the notification is indicative of the patient query data structure matching the clinical trial protocol data structure.

2. The method of claim 1, wherein the encoding rule specifies how to express a value as a regular expression based on a data value type.

3. The method of claim 1, wherein the formatting rule specifies how to express a value as a value based on a data value type.

4. The method of claim 1, wherein the structure rule specifies an order in which encoded data values and formatted data values should be concatenated.

5. The method of claim 1, further comprising:
associating the clinical trial protocol data structure with the clinical trial.

6. The method of claim 1, wherein the notification is received by the device associated with the patient via the at least one service provider computing device.

7. A method comprising:
receiving, by at least one healthcare provider computing device, unstructured criteria data associated with a clinical trial, wherein the unstructured criteria data is expressed as a plurality of values, each associated with a data value type;
determining, by the at least one healthcare provider computing device, for the plurality of values, and based on the clinical trial, an encoding rule and a formatting rule;
encoding, by the at least one healthcare provider computing device, based on the encoding rule and the corresponding data value type, a first portion of the plurality of values as encoded data values;
formatting, by the at least one healthcare provider computing device, based on the formatting rule and the corresponding data value type, a second portion of the plurality of values as formatted data values;
concatenating, by the at least one healthcare provider computing device, based on a structure rule associated with the clinical trial, the encoded data values and the formatted data values to generate a clinical trial protocol data structure;
storing, by the at least one healthcare provider computing device, the clinical trial protocol data structure in at least one database, wherein the at least one database is accessible by at least one service provider computing device associated with the at least one healthcare provider computing device;
receiving, by the at least one service provider computing device from the at least one healthcare provider computing device associated with a prescriber, a healthcare request associated with a patient;
sending, by the at least one service provider computing device, based on the healthcare request, a prescription request to at least one pharmacy computing device for processing;
determining, by the at least one service provider computing device, based on the healthcare request, patient data associated with the patient;
determining, by the at least one service provider computing device, based on the patient data and the clinical trial protocol data structure stored in the at least one database, that the patient may be a candidate for participation in the clinical trial;
receiving, by the at least one service provider computing device, based on the prescription request, a prescription response from the at least one pharmacy computing device; and
sending, by the at least one service provider computing device, a notification indicating that the patient has been identified for participation in the clinical trial and the prescription response.

8. The method of claim 7, wherein the healthcare request comprises a prior authorization request or a prescription benefit check request.

9. The method of claim 7, wherein determining, based on the healthcare request, the patient data associated with the patient comprises at least one of: extracting the patient data from the healthcare request or retrieving the patient data from an electronic health record using an identifier in the healthcare request.

10. The method of claim 7, wherein the patient data comprises at least one of: a patient identifier, a patient name, a patient sex, a patient condition, a patient age, a patient weight, a patient height, a patient race, a patient location, a medication specified by the healthcare request, or a medication indicated in an electronic health record associated with the patient.

11. The method of claim 7, wherein the encoding rule specifies how to express a value as a regular expression based on a data value type.

12. The method of claim 7, wherein the formatting rule specifies how to express a value as a value based on a data value type.

13. The method of claim 7, wherein the structure rule specifies an order in which encoded data values and formatted data values should be concatenated.

14. The method of claim 7, further comprising:
comparing a patient query data structure to one or more clinical trial protocol data structures; and
based on the comparison, identifying the clinical trial associated with a match between the patient query data structure and the one or more clinical trial protocol data structures.

15. The method of claim 7, further comprising matching the patient data with one or more portions of data associated with the clinical trial.

16. The method of claim 7, wherein sending the notification indicating that the patient has been identified for participation in the clinical trial and the prescription response causes sending a referral link to a patient computing device and pre-screening the patient for participation in the clinical trial.

17. A system comprising:
at least one healthcare provider computing device associated with a prescriber, configured to:
receive unstructured criteria data associated with a clinical trial, wherein the unstructured criteria data is expressed as a plurality of values, each associated with a data value type;
determine, for the plurality of values, and based on the clinical trial, an encoding rule and a formatting rule;
encode, based on the encoding rule and the corresponding data value type, a first portion of the plurality of values as encoded data values;
format, based on the formatting rule and the corresponding data value type, a second portion of the plurality of values as formatted data values;
concatenate, based on a structure rule associated with the clinical trial, the encoded data values and the formatted data values to generate a clinical trial protocol data structure;
send a healthcare request to a service provider computing device; and
store, in at least one database, the clinical trial protocol data structure, wherein the at least one database is accessible by at least one service provider computing device associated with the at least one healthcare provider computing device;
the at least one service provider computing device, configured to:
receive the healthcare request,
determine, based on the healthcare request, patient data associated with a patient, determine, based on the patient data and the clinical trial protocol data structure stored in the at least one database, that the patient may be a candidate for participation in the clinical trial, and
send, based on the healthcare request, a prescription request to at least one pharmacy claims processor computing device for processing;
the at least one pharmacy claims processor computing device, configured to:
receive the prescription request, and
send a prescription response to the service provider computing device; and
wherein the at least one service provider computing device, is further configured to:
receive the prescription response, and
send a notification and the prescription response to the at least one healthcare provider computing device, the notification indicating that the patient has been identified for participation in the clinical trial.

18. The system of claim 17, wherein the healthcare request comprises a prior authorization request or a prescription benefit check request.

19. The system of claim 17, wherein the at least one service provider computing device is configured to determine, based on the healthcare request, the patient data associated with the patient by extracting the patient data from the healthcare request or retrieving the patient data from an electronic health record using an identifier in the healthcare request.

20. The system of claim 17, wherein the patient data comprises at least one of: a patient identifier, a patient name, a patient sex, a patient condition, a patient age, a patient weight, a patient height, a patient race, a patient location, a medication specified by the healthcare request, a medication indicated in an electronic health record associated with the patient.

* * * * *